United States Patent
Hirano et al.

(10) Patent No.: US 10,292,996 B2
(45) Date of Patent: May 21, 2019

(54) DEOXYRIBONUCLEOSIDE MONOPHOSPATE BYPASS THERAPY FOR MITOCHONDRIAL DNA DEPLETION SYNDROME

(71) Applicant: The Trustees of Columbia University in the City of New York, New York, NY (US)

(72) Inventors: Michio Hirano, New York, NY (US); Caterina Garone, Cambridge (GB)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 363 days.

(21) Appl. No.: 15/082,207

(22) Filed: Mar. 28, 2016

(65) Prior Publication Data
US 2016/0279159 A1    Sep. 29, 2016

Related U.S. Application Data

(60) Provisional application No. 62/138,583, filed on Mar. 26, 2015.

(51) Int. Cl.
*A61K 31/708*   (2006.01)
*A61K 31/7068*  (2006.01)
*A61K 31/7072*  (2006.01)
*A61K 31/7076*  (2006.01)

(52) U.S. Cl.
CPC ........ *A61K 31/7072* (2013.01); *A61K 31/708* (2013.01); *A61K 31/7068* (2013.01); *A61K 31/7076* (2013.01)

(58) Field of Classification Search
CPC .............. A61K 31/7072; A61K 31/708; A61K 31/7068; A61K 31/7076
See application file for complete search history.

(56) References Cited

FOREIGN PATENT DOCUMENTS

WO    2016/205671 A9 * 12/2017

OTHER PUBLICATIONS (R) Bulst et al., "In vitro Supplementation with dAMP/dGMP Leads to Partial Restoration of mtDNA Levels in MItochondrial Depletion Syndrome," Human Molecular Genetics, 18(9), 1590-1599 (2009).*
Sarzi, Emmanuelle et al. (Dec. 2007) Mitochondrial DNA Depletion is a Prevalent Cause of Multiple Respiratory Chain Deficiency in Childhood. Hum Mol Genet 17:2433-2440 J. Pediatrics, 105, 531-534.
Akman, et al. (May 6, 2008) Thymidine kinase 2 (H126N) knock in mice show the essential role of balanced deoxynucleotide pools for mitochondrial DNA maintenance. Hum Mol Genet 17:2433-2440.
Alston, et al. (Dec. 3, 2013) Late-onset respiratory failure due to TK2 mutations causing multiple mtDNA deletions. Neurology. 81:2051-3.
Bartesaghi, et al. (Jan. 26, 2010) Loss of thymidine kinase 2 alters neuronal bioenergetics and leads to neurodegeneration. Hum Mol Genet. 19:1669-77.
Béhin, et al. (Feb. 28, 2012) Adult cases of mitochondrial DNA depletion due to TK2 defect An expanding spectrum. Neurology 78:644-648.
Blakely, et al. (Apr. 14, 2008) Novel mutations in the TK2 gene associated with fatal mitochondrial DNA depletion myopathy. Neuromuscular Disorders 18:557-560.
Bourdon, et al. (May 7, 2007) Mutation of RRM2B, encoding p53-controlled ribonucleotide reductase (p53R2), causes severe mitochondrial DNA depletion. Nat Genet 39: 776-780.
Brown, Bicknell. (Aug. 15, 1998) Thymidine phosphorylase, 2-deoxy-D-ribose and angiogenesis. Biochem J 334: 1-8.
Carrozzo, et al. (Jan. 30, 2003) Mutation analysis in 16 patients with mtDNA depletion. Hum Mutat 21:453-454.
Chanprasert, et al. (Jul. 10, 2013) Molecular and clinical characterization of the myopathic form of mitochondrial DNA depletion syndrome caused by mutations in the thymidine kinase (TK2) gene. Mol Genet Metab. 110:153-61.
Chanprasert, et al. (Dec. 6, 2012) TK2-Related Mitochondrial DNA Depletion Syndrome, Myopathic Form. GeneReviews® Internet.
Collins, et al. (Aug. 4, 2009) Progressive myofiber loss with extensive fibro-fatty replacement in a child with mitochondrial DNA depletion syndrome and novel thymidine kinase 2 gene mutations. Neuromuscular Disorders 19:784-787.
Copeland (Mar. 21, 2008) Inherited mitochondrial diseases of DNA replication. Ann. Rev. Med. 59:131-146.
DiMauro, et al. (Feb. 20, 1987) Cytochrome c oxidase deficiency in Leigh syndrome. Ann Neurol 22: 498-506.
DiMauro, Schon. (Jul. 1, 2003) Mitochondrial respiratory-chain diseases. N Engl J Med 348:2656-2668.
DiMauro, Hirano. (2005) Mitochondrial encephalomyopathies: an update. Neuromuscul Disord 15:276-286. Accepted Dec. 10, 2004.
Dorado, et al. (2011) Onset and organ specificity of Tk2 deficiency depends on Tk1 down-regulation and transcriptional compensation. Hum Mol Genet. 20:155-64. Accepted Oct. 6, 2010.
Elpeleg, et al. (Apr. 7, 2005) Deficiency of the ADP-forming succinyl-CoA synthase activity is associated with encephalomyopathy and mitochondrial DNA depletion. Am J Hum Genet 76: 1081-1086.
Ferraro, et al. (2010) Quantitation of cellular deoxynucleoside triphosphates. Nucleic Acids Research 38: e85. Accepted Nov. 18, 2009.
Galbiati, et al. (2006) New mutations in TK2 gene associated with mitochondrial DNA depletion. Pediatr Neurol 34: 177-185. Accepted Jul. 11, 2005.

(Continued)

*Primary Examiner* — Lawrence E Crane
(74) *Attorney, Agent, or Firm* — Leason Ellis LLP

(57) ABSTRACT

The present invention provides a pharmacological therapy using deoxyribonucleoside monophosphate compounds, or mixtures thereof, for the treatment of human genetic diseases. The compounds of the present invention can be used to treat mitochondrial DNA depletion syndromes or other disorders of unbalanced nucleotide pools, such as thymidine kinase 2 (TK2) deficiency.

25 Claims, 30 Drawing Sheets

(56) References Cited

OTHER PUBLICATIONS

Garone, et al (Jun. 26, 2014) Deoxypyrimidine monophosphate bypass therapy for thymidine kinase 2 deficiency. EMBO Mol Med 6:1016-1027.

Gotz, et al. (Sep. 3, 2008) Thymidine kinase 2 defects can cause multi-tissue mtDNA depletion syndrome. Brain 131:2841-2850.

Hirano, et al. (Dec. 2001) Defects of intergenomic communication: autosomal disorders that cause multiple deletions and depletion of mitochondrial DNA. Semin Cell Develop Biol 12:417-427.

Leshinsky-Silver, et al. (2008) A defect in the thymidine kinase 2 gene causing isolated mitochondrial myopathy without mtDNA depletion. Eur J Paediatr Neurol 12:309-13. Accepted Sep. 2, 2007.

Lesko, et al. (2010) Two novel mutations in thymidine kinase-2 cause early onset fatal encephalomyopathy and severe mtDNA depletion. Neuromuscul Disord 20:198-203. Accepted Nov. 25, 2009.

Lopez, et al. (2009) Unbalanced deoxynucleotide pools cause mitochondrial DNA instability in thymidine phosphorylase deficient mice. Hum Mol Genet 18: 714-722. Accepted Nov. 19, 2008.

Mancuso, et al. (Jun. 20, 2002) Mitochondrial DNA depletion: mutations in thymidine kinase gene with myopathy and SMA. Neurology. 59:1197-202.

Mancuso, et al. (Jul. 2003) Mitochondrial myopathy of childhood associated with mitochondrial DNA depletion and a homozygous mutation (T77M) in the TK2 gene. Arch Neurol. 60:1007-9.

Mandel, et al. (Nov. 2001) The deoxyguanosine kinase gene is mutated in individuals with depleted hepatocerebral mitochondrial DNA. Nat Genet 29: 337-341.

Martí, et al. (Apr. 8, 2010) Hearing loss in a patient with the myopathic form of mitochondrial DNA depletion syndrome and a novel mutation in the TK2 gene. Pediatr Res. 68:151-4.

Martí, et al. (2012) Measurement of mitochondrial dNTP pools. Methods Mol Biol 837: 135-148. Dec. 20, 2011.

Martí, et al. (Jul. 2003) Alterations of nucleotide metabolism: a new mechanism for mitochondrial disorders. Clin Chem Lab Med. 41:845-51.

Naviaux, Nguyen. (Feb. 4, 2004) POLG mutations associated with Alpers' syndrome and mitochondrial DNA depletion. Ann Neurol 55: 706-712.

Oskoui, et al. (Aug. 2006) Clinical spectrum of mitochondrial DNA depletion due to mutations in the thymidine kinase 2 gene. Arch Neurol 63:1122-1126.

Ostergaard, et al. (Apr. 26, 2007) Deficiency of the alpha subunit of succinate-coenzyme A ligase causes fatal infantile lactic acidosis with mitochondrial DNA depletion. Am J Hum Genet 81: 383-387.

Paradas, et al. (2012) TK2 mutation presenting as indolent myopathy. Neurology 29:504-506. Jan. 9, 2013.

Roos, et al. (May 20, 2014) Mitochondrial DNA depletion in single fibers in a patient with novel TK2 mutations. Neuromuscul Disord. 24:713-20.

Saada, et al. (Oct. 22, 2001) Mutant mitochondrial thymidine kinase in mitochondrial DNA depletion myopathy. Nat Genet 29:342-344.

Saada, et al. (Aug. 7, 2003) Mitochondrial deoxyribonucleoside triphosphate pools in thymidine kinase 2 deficiency. Biochem Biophys Res Commun 310:963-966.

Sarzi, et al. (May 2007) Twinkle helicase (PEO1) gene mutation causes mitochondrial DNA depletion. Ann Neurol. 62: 579-587.

Spinazzola, et al. (Apr. 2, 2006) MPV17 encodes an inner mitochondrial membrane protein and is mutated in infantile hepatic mitochondrial DNA depletion. Nat Genet 38: 570-575.

Tulinius, et al. (Mar. 6, 2005) Novel mutations in the thymidine kinase 2 gene (TK2) associated with fatal mitochondrial myopathy and mitochondrial DNA depletion. Neuromuscul Disord. 15:412-415.

Tyynismaa, et al. (2012) Thymidine kinase 2 mutations in autosomal recessive progressive external ophthalmoplegia with multiple mitochondrial DNA deletions. Hum Mol Genet 21:66-75. Accepted Sep. 19, 2011.

Vilà, et al. (Apr. 2003) Reversion of mtDNA depletion in a patient with TK2 deficiency. Neurology 60:1203-1205.

Wang, et al. (2005) Molecular insight into mitochondrial DNA depletion syndrome in two patients with novel mutations in the deoxyguanosine kinase and thymidine kinase 2 genes. Mol Genet Metab. 84:75-82. Available online Nov. 11, 2004.

* cited by examiner

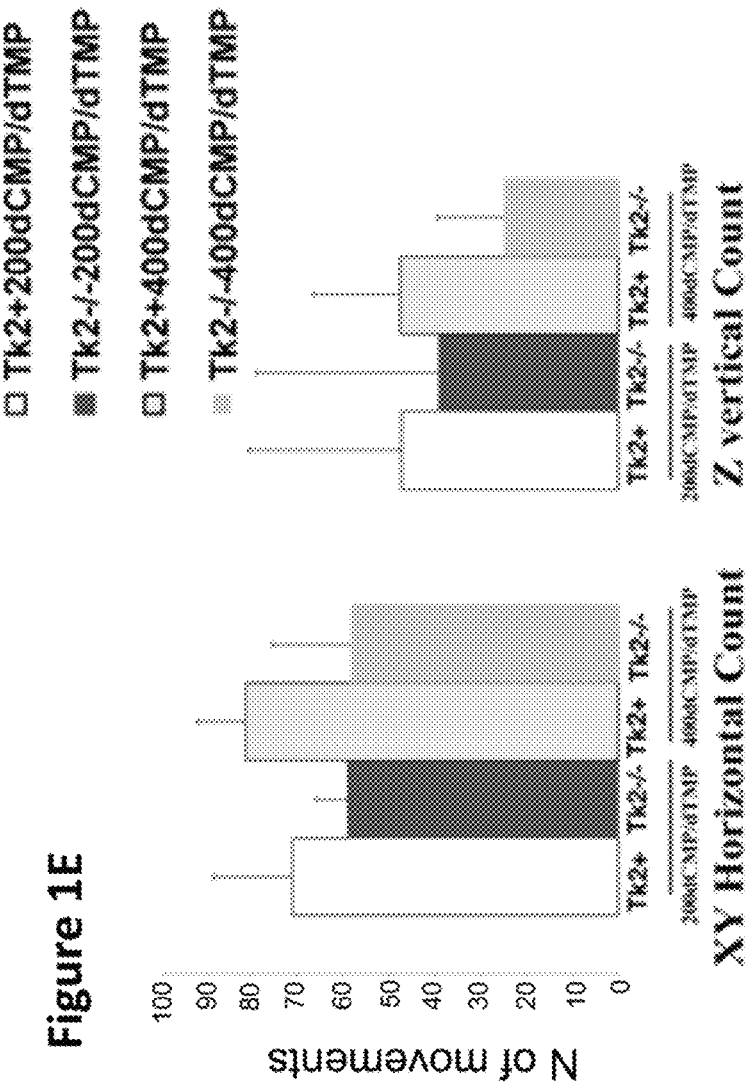

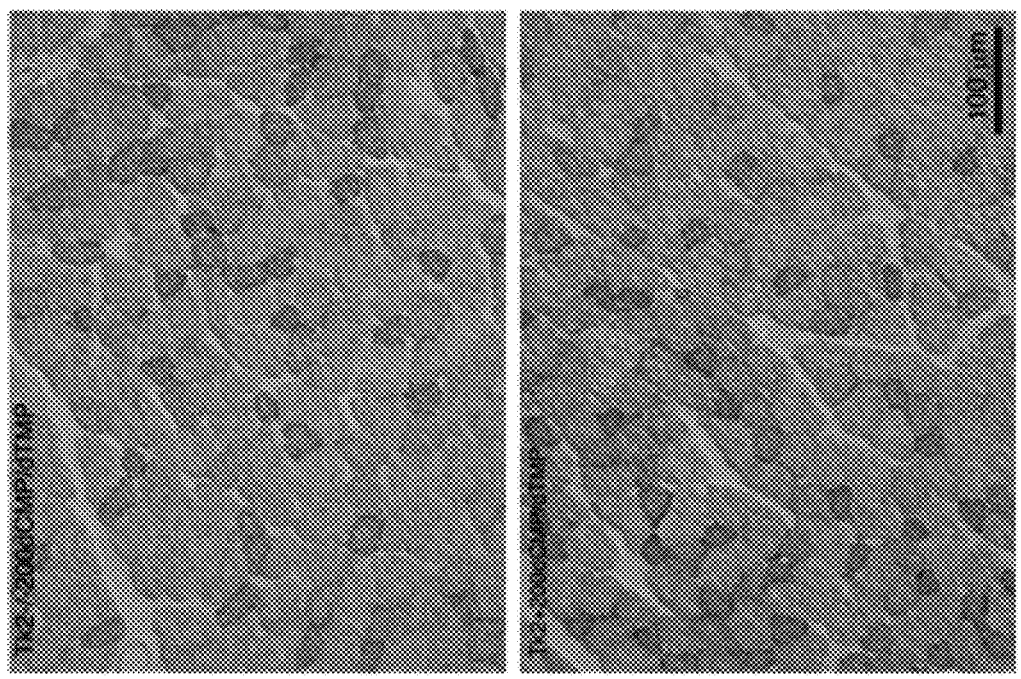

Figure 2F

Mitochondrial respiratory chain activities

| Normalized to mg-protein | Tk2⁻/⁻²⁰⁰dCMP/dTMP | Tk2⁻/⁻²⁰⁰dCMP/dTMP |
|---|---|---|
| I | 0.60±0.14 | 0.47±0.07 |
| IV | 1.22±0.3 | 1.29±0.3 |
| II+III | 0.14±0.09 | 0.33±0.1 |
| II | 0.14±0.08 | 0.30±0.1 |
| CS | 6.37±0.5 | 7±1 |
| Normalized to CS | Tk2⁻/⁻²⁰⁰dCMP/dTMP | Tk2⁻/⁻²⁰⁰dCMP/dTMP |
| I | 0.1±0.03 | 0.07±0.02 |
| IV | 0.2±0.03 | 0.18±0.03 |
| II+III | 0.048±0.02 | 0.046±0.01 |
| II | 0.023±0.01 | 0.04±0.008 |

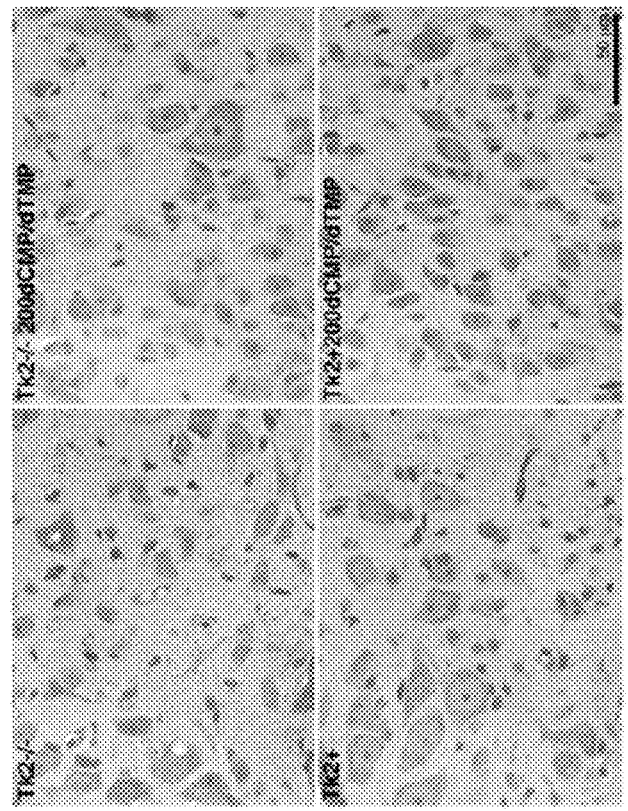
Figure 3
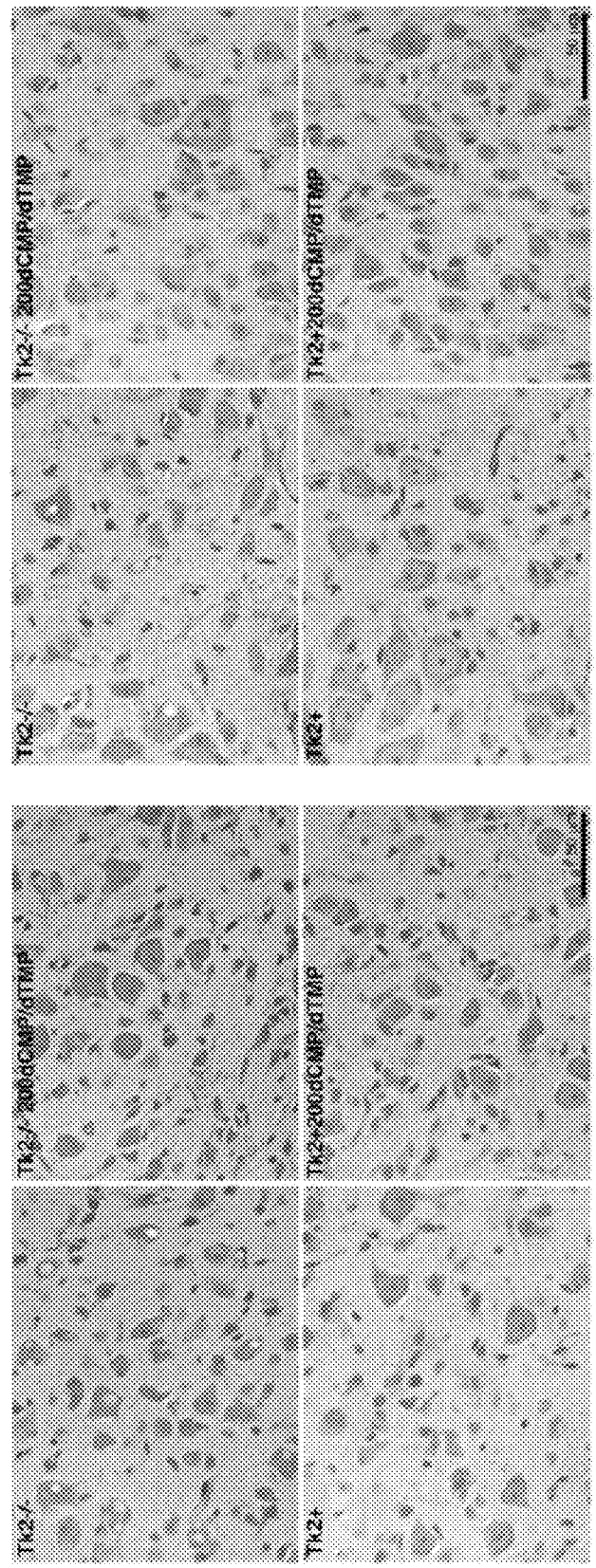
Figure 3A BRAIN
Figure 3B SPINAL CORD

Figure 4
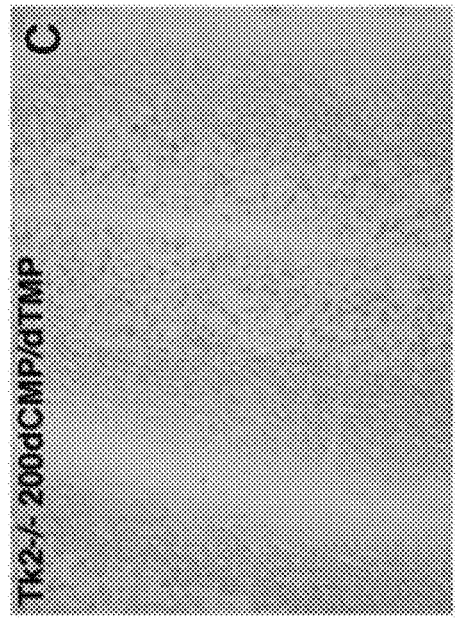
Figure 4A
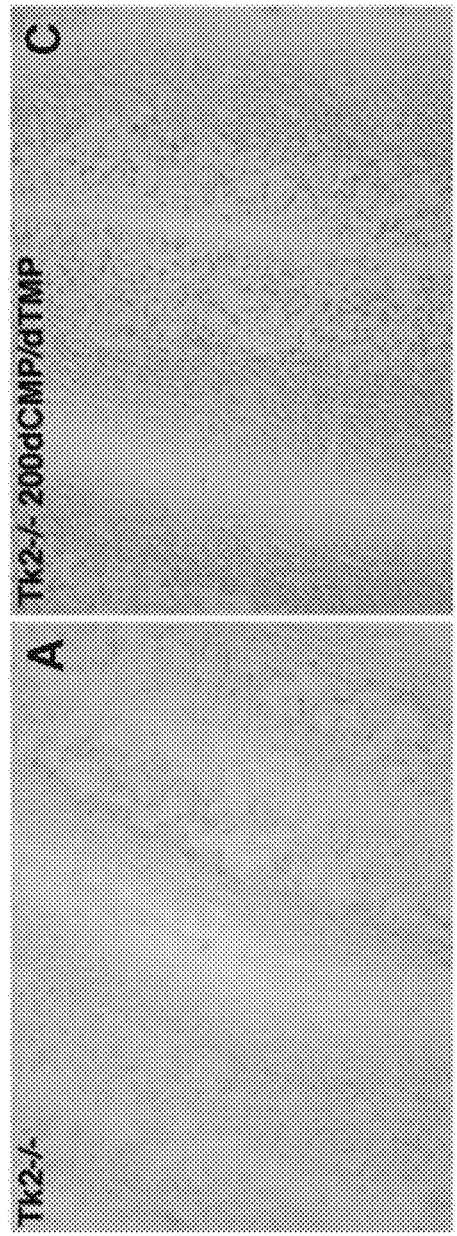
Figure 4B
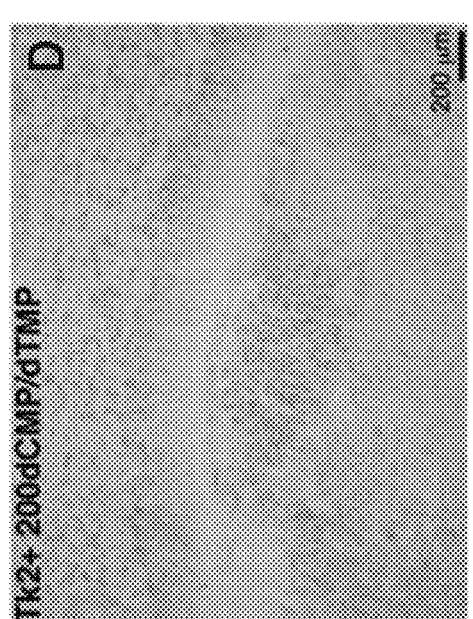
Figure 4C
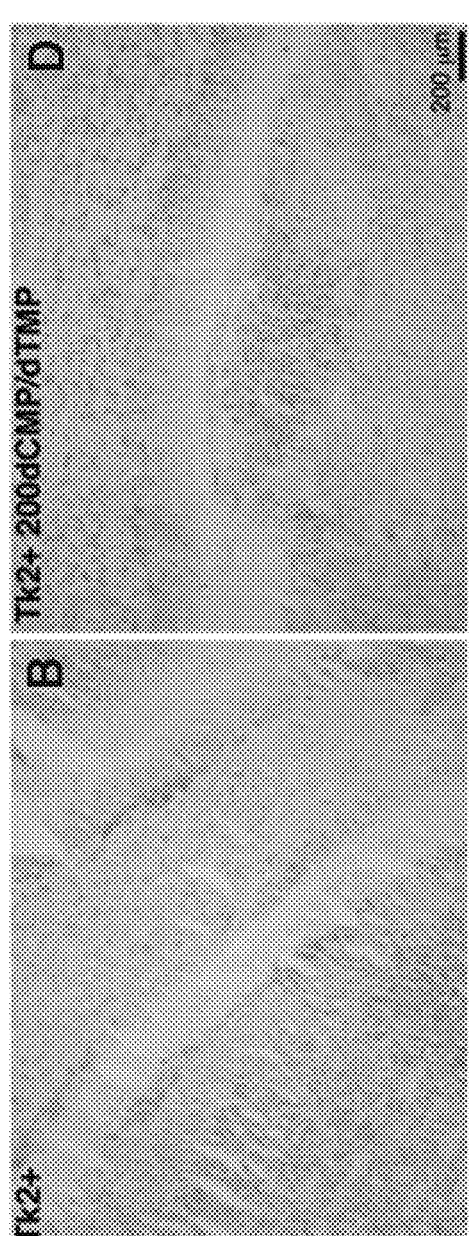
Figure 4D

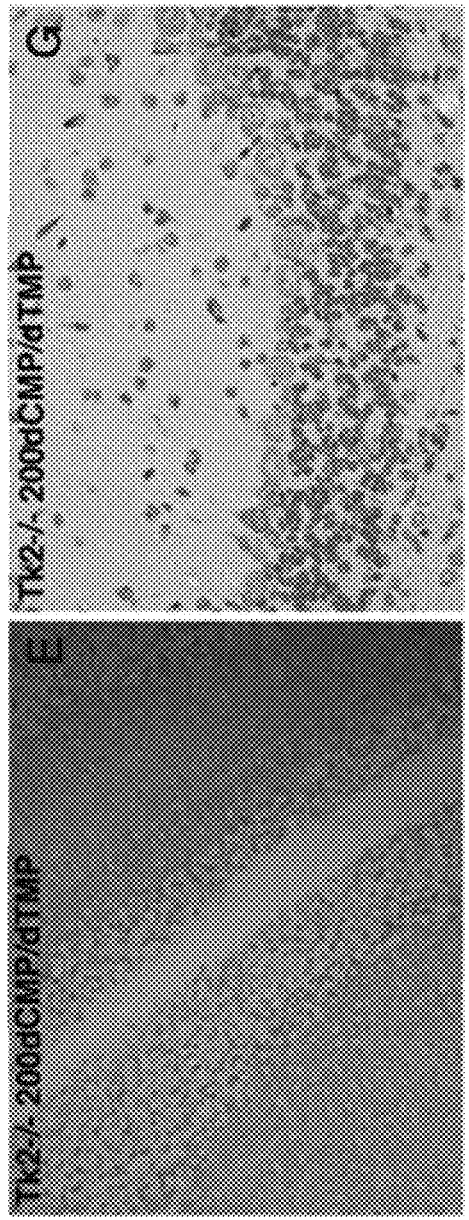
Figure 4E
Figure 4G
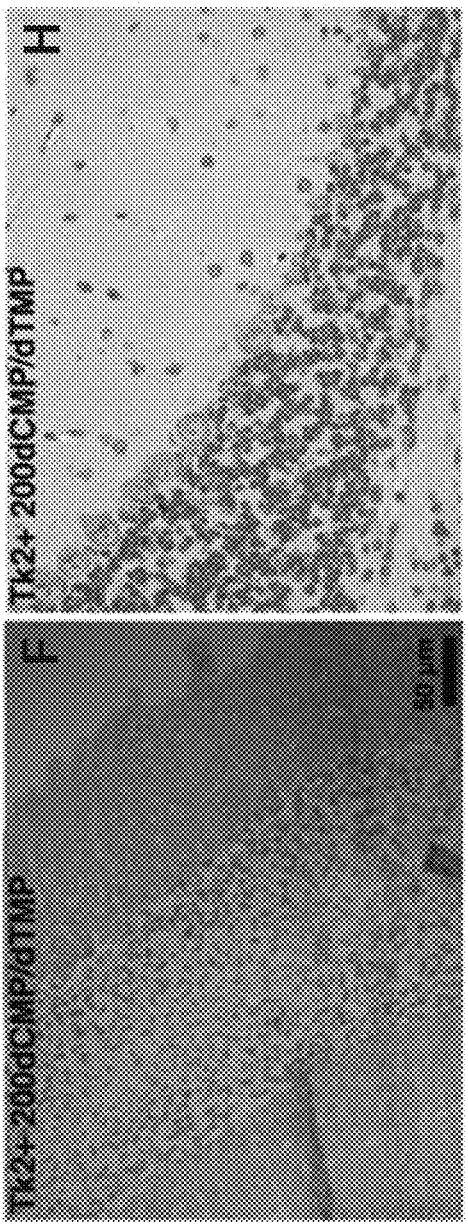
Figure 4F
Figure 4H

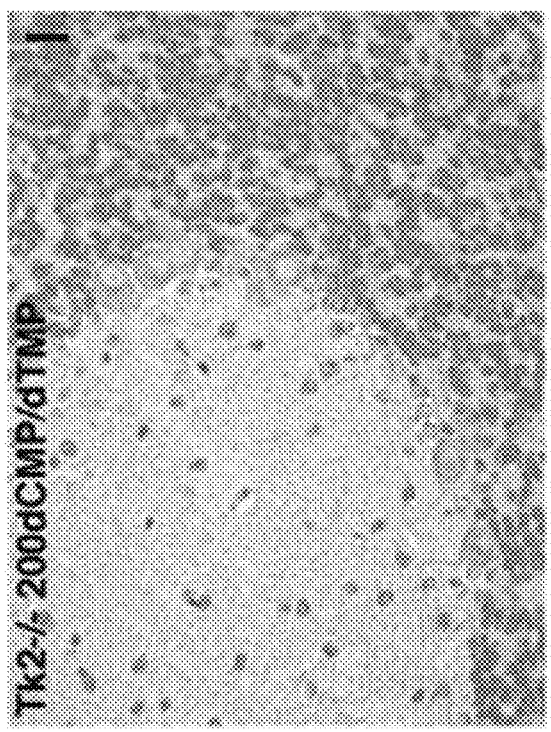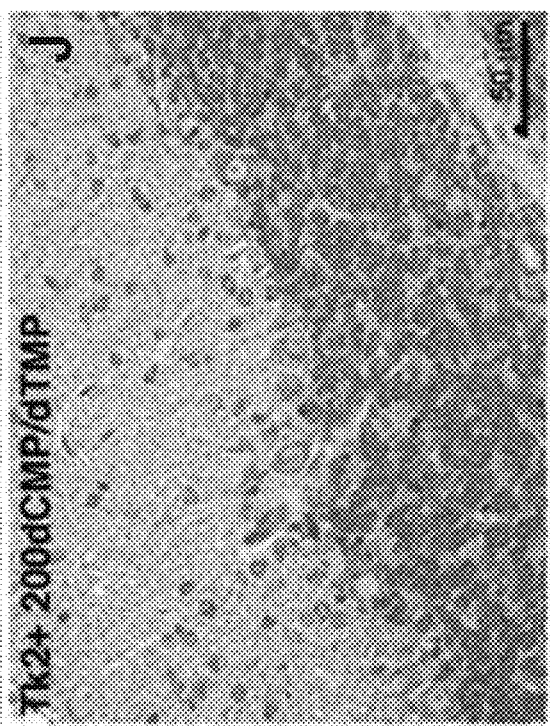
Figure 4I
Figure 4J

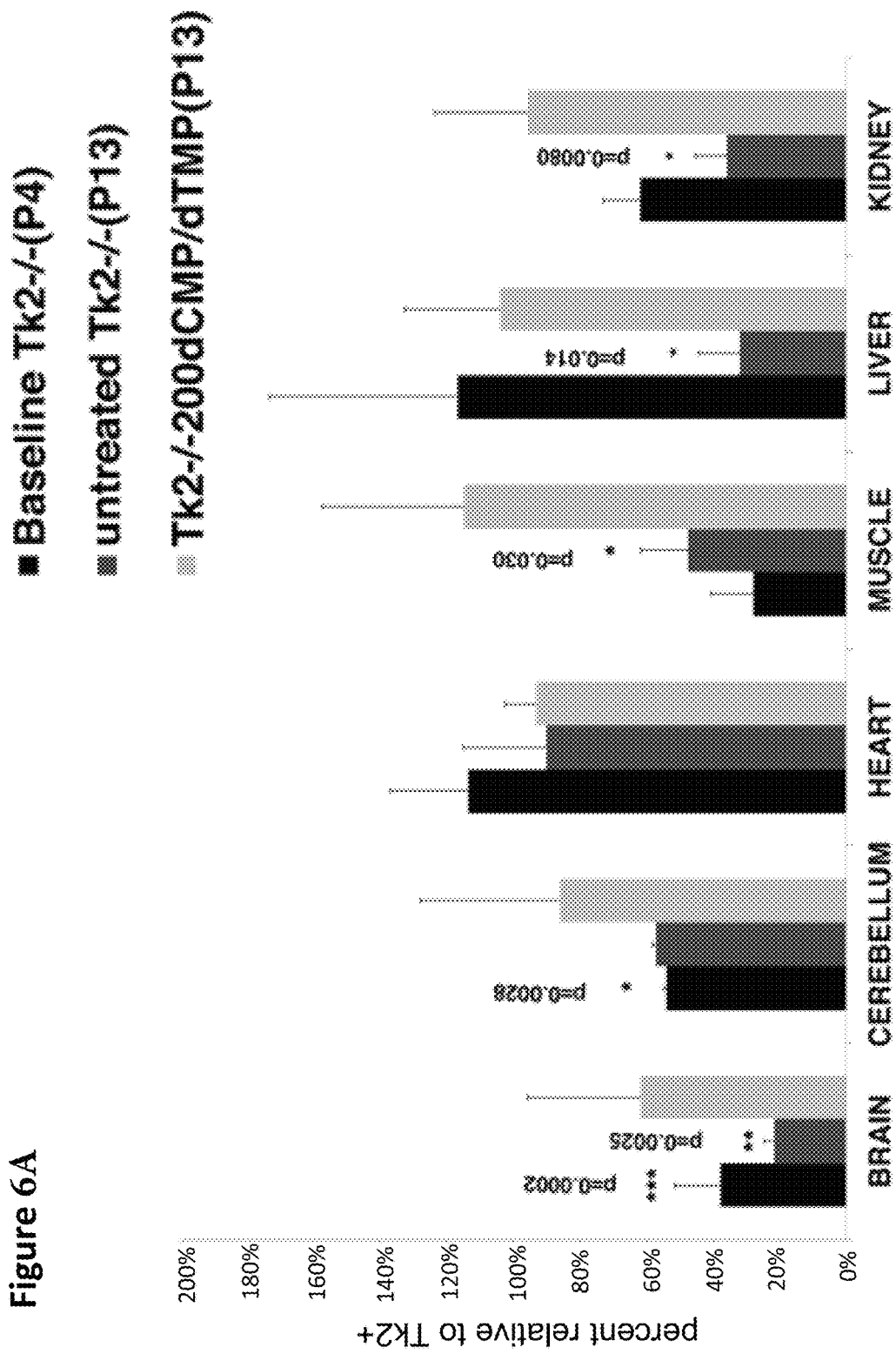

Figure 7
BRAIN CEREBRUM
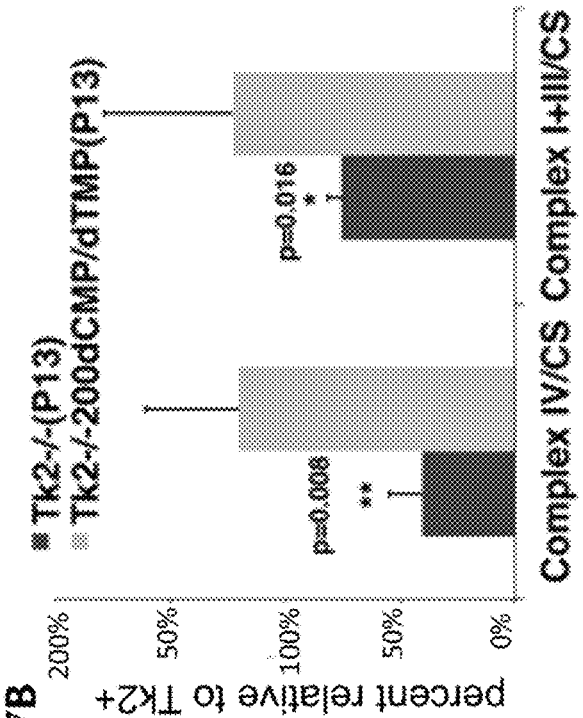
Figure 7A
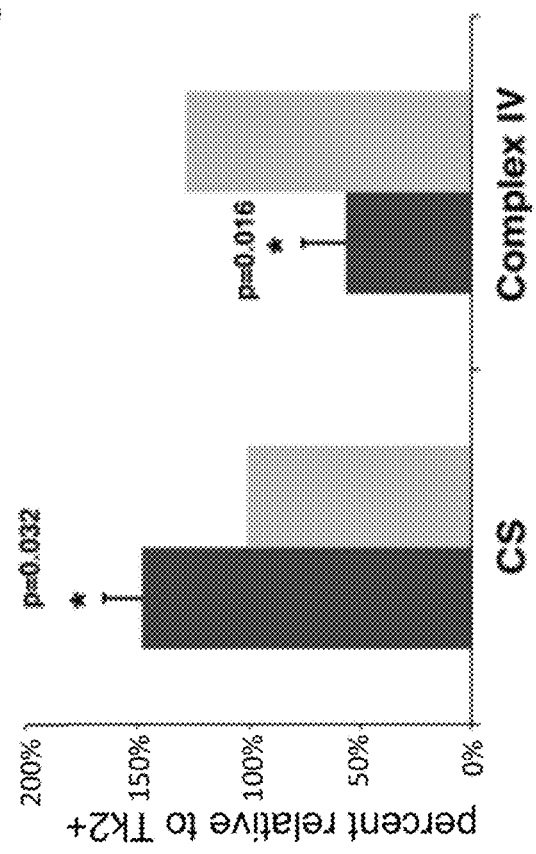
Figure 7B

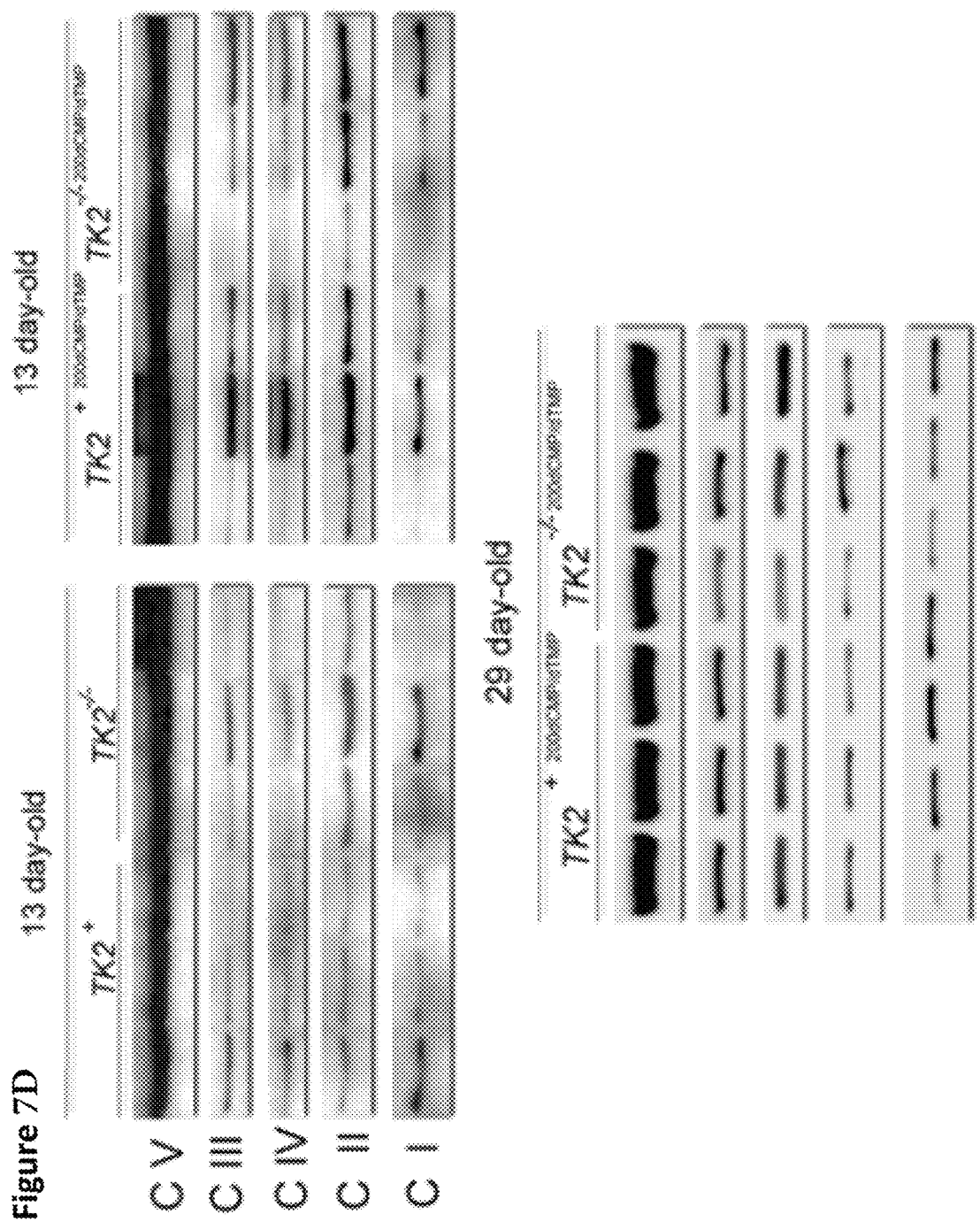

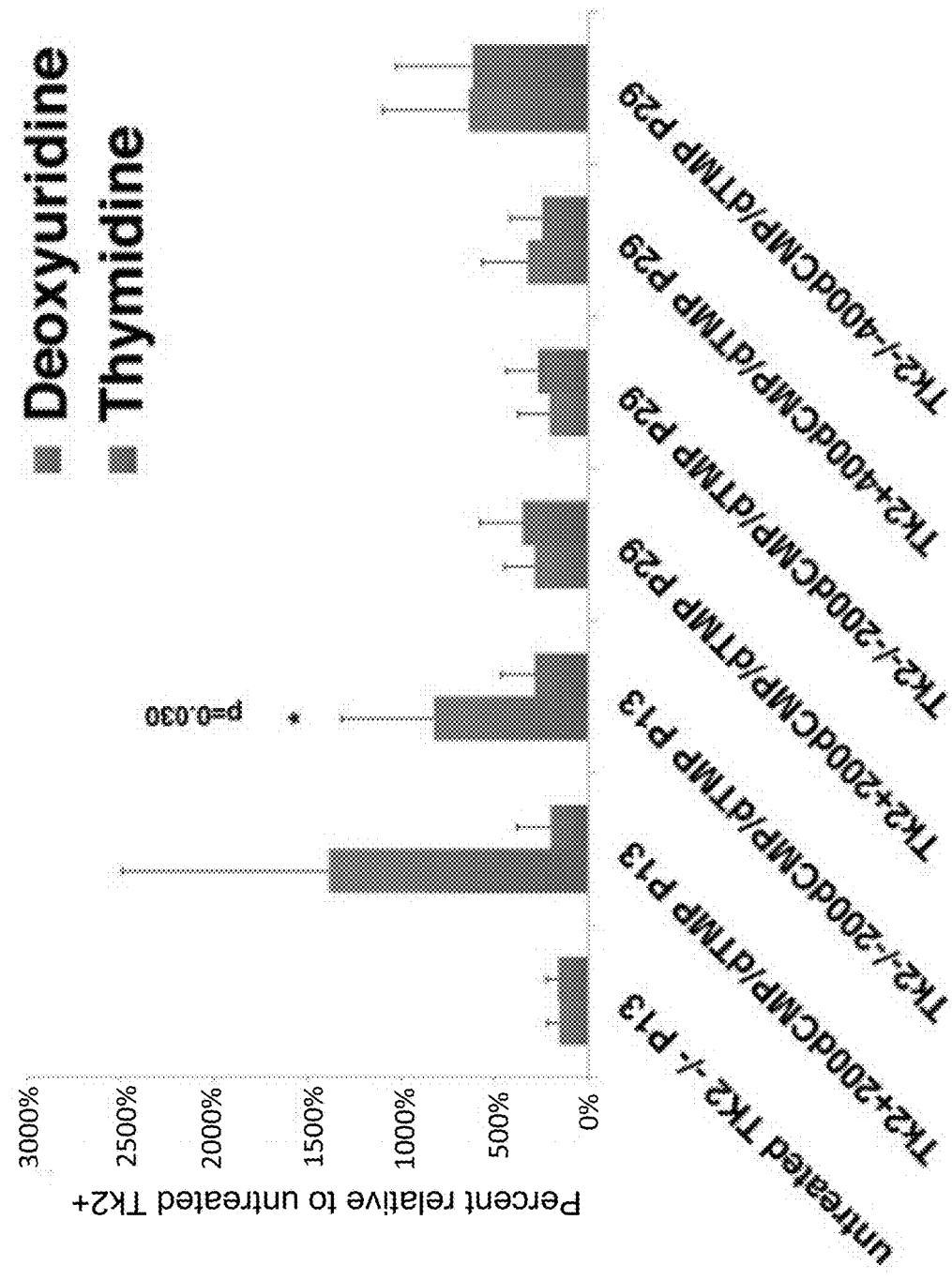

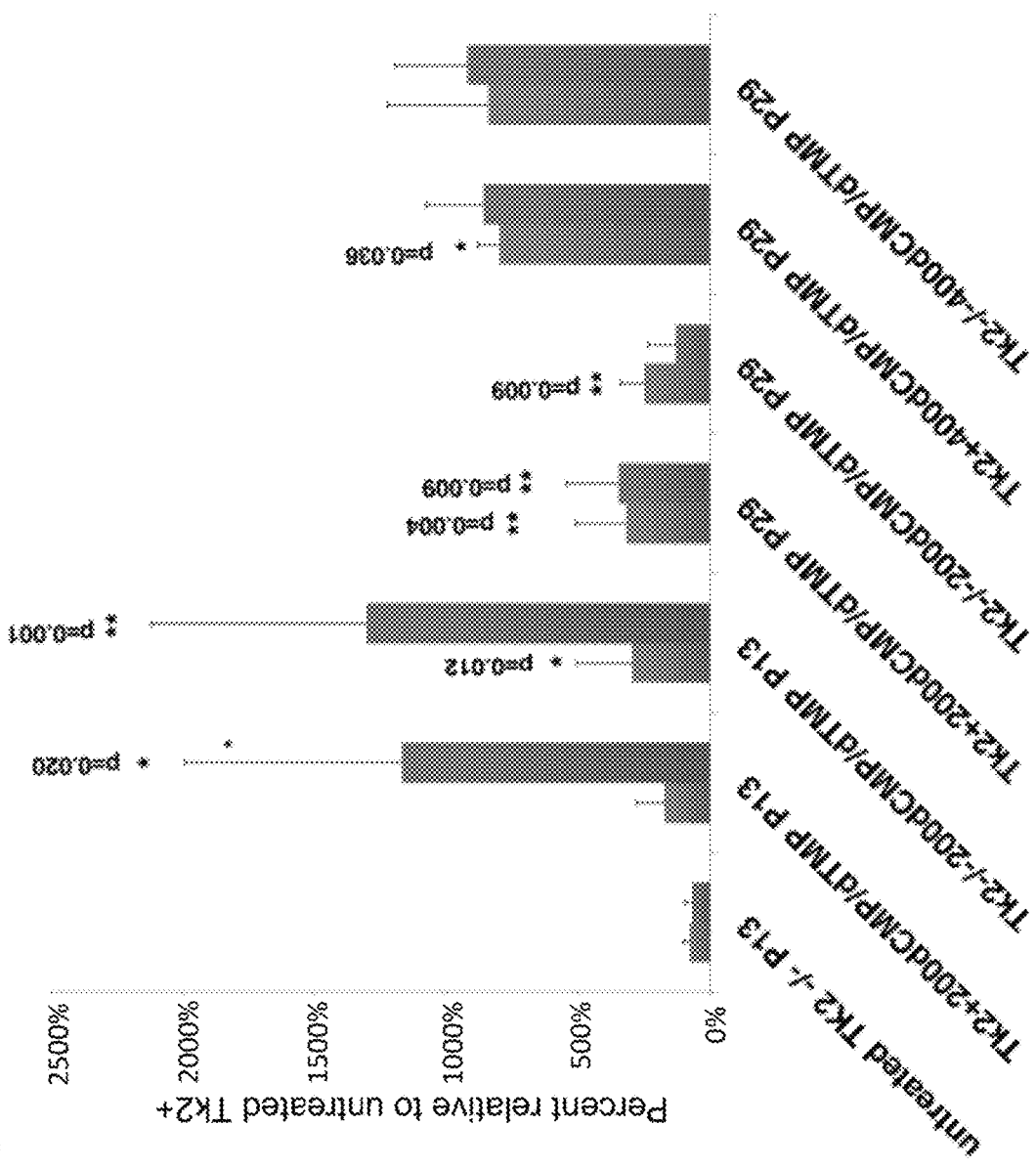

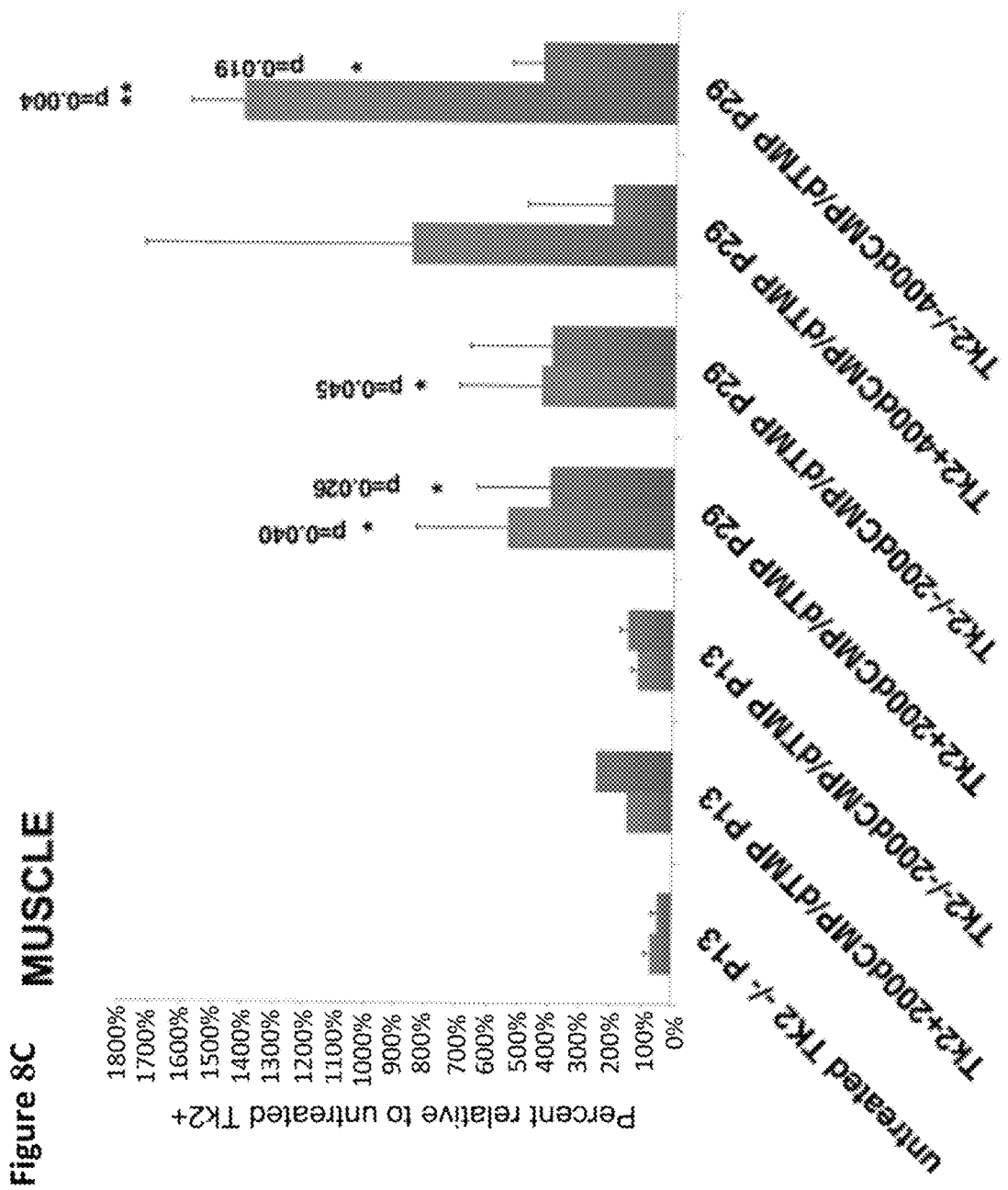
Figure 8C  MUSCLE

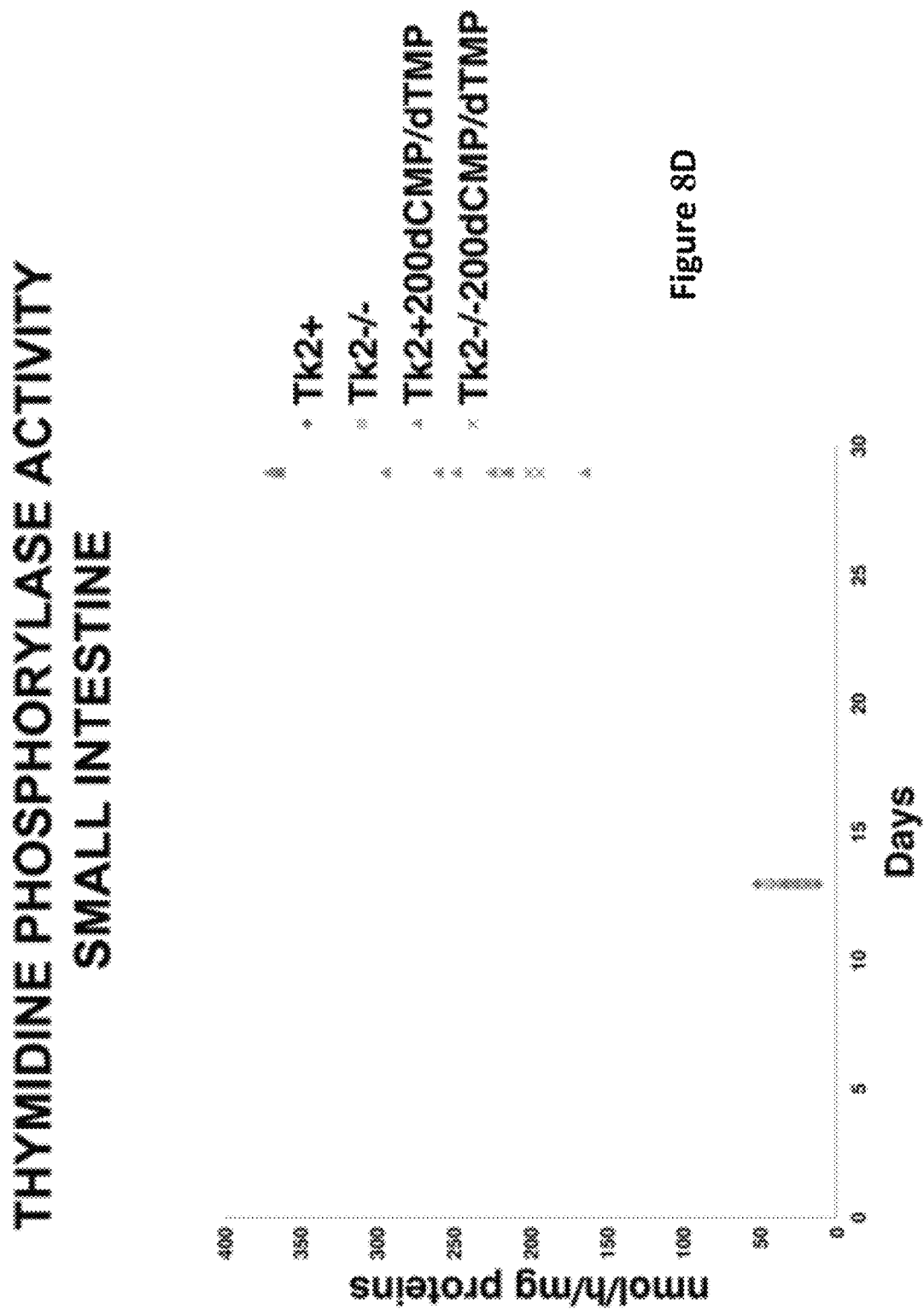

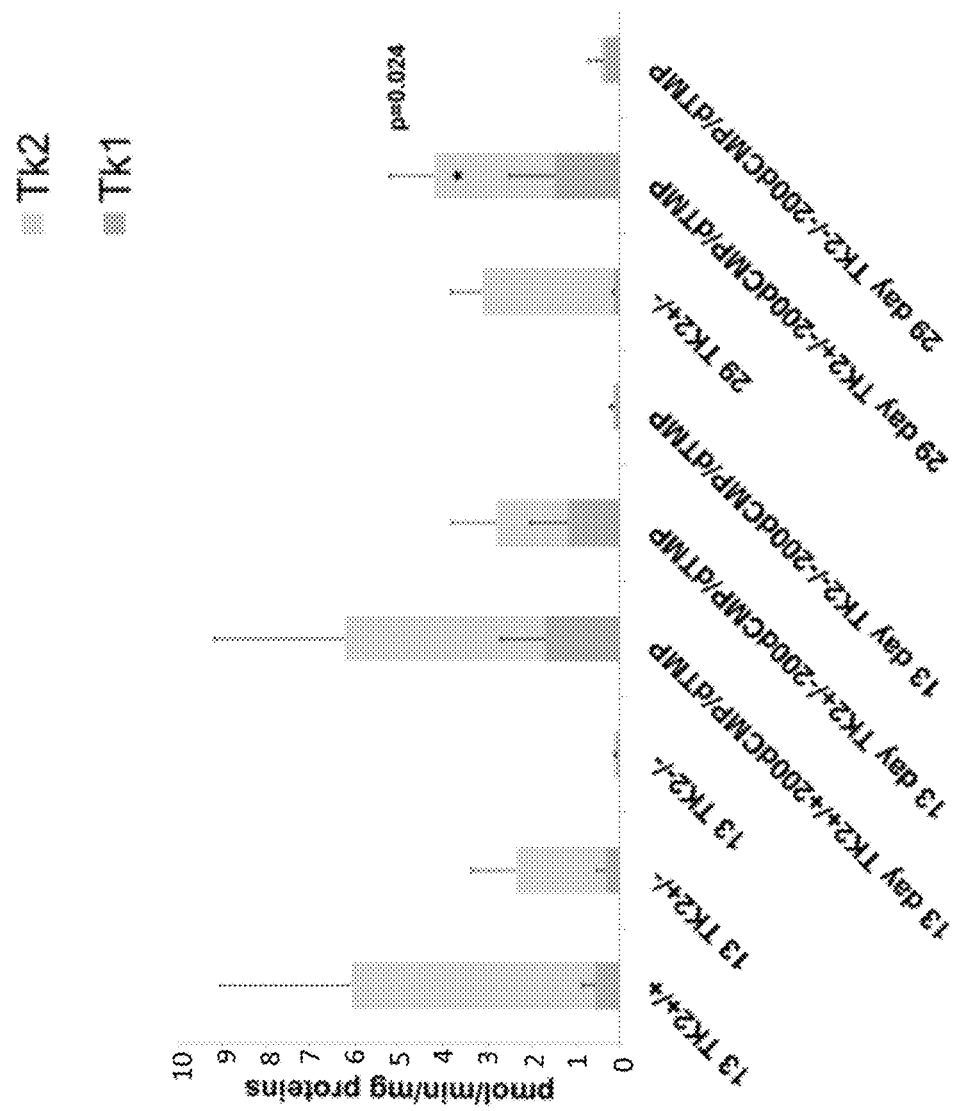
Figure 8E  BRAIN

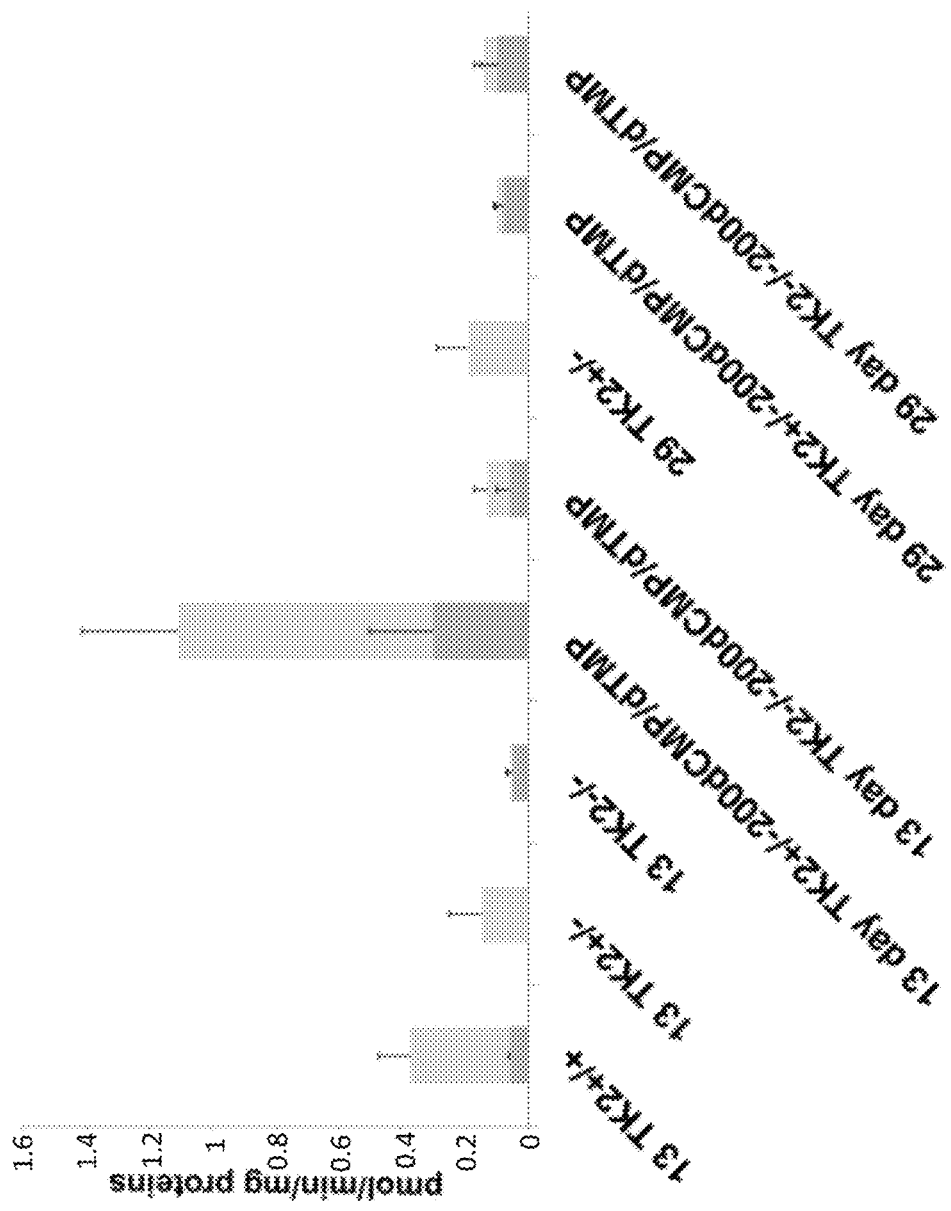
Figure 8F MUSCLE

DEOXYRIBONUCLEOSIDE MONOPHOSPATE BYPASS THERAPY FOR MITOCHONDRIAL DNA DEPLETION SYNDROME

CROSS-REFERENCE TO RELATED APPLICATIONS

The present application claims priority to U.S. provisional patent application Ser. No. 62/138,583 filed Mar. 26, 2015, which is hereby incorporated by reference in its entirety.

GOVERNMENT SUPPORT CLAUSE

This invention was made with government support under grant P01HD080642 awarded by the NIH. The Government has certain rights in this invention.

FIELD OF THE INVENTION

The invention relates generally to a pharmacological therapy for a human genetic diseases, specifically mitochondrial DNA depletion syndromes, and more specifically, thymidine kinase 2 (TK2) deficiency. The pharmacological therapy involves the administration of at least one deoxyribonucleoside monophosphate, or mixtures thereof. For the treatment of TK2 deficiency, the pharmacological therapy involves the administration of either deoxythymidine monophosphate (dTMP) or deoxycytidine monophosphate (dCMP), or mixtures thereof. This molecular bypass approach is applicable to other disorders of unbalanced nucleotide pools, especially those found in mitochondrial DNA depletion syndrome.

BACKGROUND OF THE INVENTION

Mitochondrial diseases are clinically heterogeneous diseases due to defects of the mitochondrial respiratory chain and oxidative phosphorylation, the biochemical pathways that converts energy in electrons into adenosine triphosphate (ATP). The respiratory chain is comprised of four multi-subunit enzymes (complexes I-IV) that transfer electrons to generate a proton gradient across the inner membrane of mitochondria and the flow of protons through complex V drives ATP synthesis (DiMauro and Schon 2003; DiMauro and Hirano 2005). Coenzyme Q10 (CoQ10) is an essential molecule that shuttles electrons from complexes I and II to complex III. The respiratory chain is unique in eukaryotic, e.g., mammalian, cells by virtue of being controlled by two genomes, mitochondrial DNA (mntDNA) and nuclear DNA (nDNA). As a consequence, mutations in either genome can cause mitochondrial diseases. Most mitochondrial diseases affect multiple body organs and are typically fatal in childhood or early adult life. There are no proven effective treatments for mitochondrial diseases. CoQ10 and its analogs have been administered to patients with mitochondrial disease to enhance respiratory chain activity and to detoxify reactive oxygen species (ROS) that are toxic by-products of dysfunctional respiratory chain enzymes.

An important subgroup of mitochondrial diseases is mitochondrial DNA depletion syndrome (MDS), which encompasses clinically and genetically heterogeneous disorders with reduction of mitochondrial DNA (mtDNA) copy number in tissues, leading to insufficient synthesis of mitochondrial respiratory chain complexes (RC) (Hirano et al., 2001). Mutations in several nuclear genes have been identified as causes of infantile MDS, including TK2, DGUOK, POLG, POLG2, SLC25A4, MPV17, RRM2B, SUCLA2, SUCLG1, TYMP, OPA1, and C10orf2 (PEO1) (Bourdon, et al. 2007; Copeland 2008; Elpeleg, et al. 2005; Mandel, et al. 2001; Naviaux and Nguyen 2004; Ostergaard, et al. 2007; Saada, et al. 2003; Sarzi, et al. 2007; Spinazzola, et al, 2006).

One of these genes s is TK2 which encodes thymidine kinase (TK2), a mitochondrial enzyme required for the phosphorylation of the pyrimidine nucleosides (deoxythymidine and deoxycytidine) to generate deoxythymidine monophosphate (dTMP) and deoxycytidine monophosphate (dCMP) (Saada, et al. 2001). Thus, mutations in TK2 impair the mitochondrial nucleoside/nucleotide salvage pathways required for synthesis of deoxynucleotide triphosphate (dNTP), the building blocks for mtDNA replication and repair.

TK2 deficiency was first described in 2001 by Saada and colleagues (Saada, et al. 2001), in four affected children originating from four different families, who suffered from severe, devastating myopathy. After an uneventful early development, at ages 6-36 months the patients developed hyperCKemia, severe muscle hypotonia with subsequent loss of spontaneous activity. Depletion of mtDNA was identified in muscle tissue with 16-22% of residual mtDNA. The patients harbored recessive TK2 mutations causing severe reductions in TK2 activity. As a consequence of mtDNA depletion, enzymatic activities of complexes I, III, IV and V of the mitochondrial respiratory chain in muscle were significantly reduced, whereas the activity of complex II, the only complex that does not contain mtDNA-encoded proteins, was relatively normal. The disease was rapidly progressive and two patients were mechanically ventilated at 3 year, while two other patients were already dead by the time of the report.

After the first description, sixty additional patients have been reported in literature and at least twenty-six further patients have been diagnosed but not reported (Alston, et al. 2013; Bartesaghi, et al. 2010; Behin, et al. 2012; Blakely, et al. 2008; Carrozzo, et al. 2003; Chanprasert, et al. 2013; Collins, et al. 2009; Galbiati, et al. 2006; Gotz, et al. 2008; Leshinsky-Silver, et al. 2008; Lesko, et al. 2010; Mancuso, et al. 2002; Mancuso, et al. 2003; Marti, et al. 2010; Oskoui, et al. 2006; Paradas, et al. 2012; Roos, et al. 2014; Tulinius, et al. 2005; Tyynismaa, et al. 2012; Vilà, et al. 2003; Wang, et al. 2005). All ninety patients had proximal muscle weakness with mild to severe respiratory insufficiency and an increased creatine kinase level up to 20-fold above normal. Disease onset ranged from birth to 74 years of age, but the majority of patients had infantile (less than 1 year, 34.4%) or childhood onset (1-12 years, 46.6%) weakness. Adult-onset (18 years or older) was reported in 14.4% of patients while only 2.2% showed first disease symptoms in adolescence (12-17 years). Global motor function was severely impaired in 47/58 (81% with Karnofsky or Lansky Performance Status <50): 46 had motor regression and were wheelchair-bound at the last follow-up while one never acquired the ability to walk. Twelve patients (3 children, 9 adults; 19%) had motor function compatible with nearly normal daily life at the last follow-up. They were able to walk independently, but required support for long distance, climbing stairs, or both. Data from motor rating scale were not available for 31 patients. Respiratory muscles were severely compromised in 30/48 (62.5%) patients, who required mechanical ventilation or nocturnal/continuous non-invasive ventilation (data were not available in 42 patients). Other muscular functions were affected in 31/83 (37.3%) patients who manifested a variable combinations of: dysarthria/dysphasia (3); rigid spine (1); mild dysphagia (9); facial diplegia (19); ptosis (22); and progressive external ophthalmoparesis (PEO) (12). Sixteen patients required gastrostomy tube because of severe dysphagia and failure to thrive. Central nervous system was affected in 13 out of 90 (14.5%) causing: recurrent seizures (6); encephalopathy (5); cognitive impairment (4); coma episodes (1); and sensorineural hearing loss (3). TK2 deficiency caused death in the first 3 years of life in 50% of the patients; 24/41 (58.5%) had infantile-onset while 7/41 (17%) had a childhood onset. Only 6.25% of patients have lived more than 42 years.

Nerve conduction studies (NCSs) and electromyography (EMG), performed in 40 patients, showed: myopathic changes defined by polyphasic short duration low amplitude motor units potentials in 32/40 (80%); "myopathic and neuropathic" changes in 3/40 (7.5%); sensory axonal neuropathy by NCS in one (2.5%); chronic denervation by EMG in another patient (2.5%); low amplitude in the facial nerve in one patient (2.5%); isolated "neuropathic" changes, in 2/40 (5%); and no abnormalities in three patients (7.5%). Muscle biopsies revealed variable depletion and multiple deletions of mitochondrial DNA (mtDNA).

Based on clinical and molecular genetics findings, three disease presentations were identified: i) infantile myopathy (37.8%) with onset of weakness in the first year of life with severe mtDNA depletion and early mortality; ii) childhood SMA-like myopathy (35.6%) with severe mtDNA depletion; and iii) adult myopathy (26.7%) with mild weakness at onset and slow progression to loss of ambulation, respiratory insufficiency, or both, often with chronic progressive external ophthalmoparesis in adulthood in association with mtDNA multiple deletions, reduced mtDNA copy number, or both. Thus, TK2 deficiency manifests a wide clinical and molecular genetic spectrum with the majority of patients manifesting in early childhood with a devastating clinical course, while others have slowly progressive weakness over decades.

Histological and histochemical study showed type I fiber prevalence, atrophic fibers with lipid storage and increased connective tissue, ragged red fibers, cytochrome c oxidase (COX, complex IV) negative fibers with succinate dehydrogenase (SDH, complex II) hyperactivity. In the end stage, muscle is replaced by fatty tissue, including the respiratory muscle, as evident in the chest MRI of one patient (Collins, et al. 2009).

Recently, adult cases have been reported, four with slowly progressive myopathy and two with PEO. In these patients the levels of mtDNA depletion was not severe and was associated with multiple deletions of mtDNA (Béhin, et al. 2012; Paradas, et al. 2012; Tyynismaa, et al. 2012).

Treatment for TK2 deficiency, like most MDS and mitochondrial disorders, has been limited to supportive therapies. Thus, there is a need for better therapeutic intervention, and understanding the pathomechanism of MDS would allow the design of treatment strategies targeting either the cause of the disease or the downstream metabolic defects, making for more effective therapies.

SUMMARY OF THE INVENTION

In certain embodiments, the present invention relates to a method of treating a disorder characterized by unbalanced nucleotide pools, comprising administering to a subject in need thereof a therapeutically effective amount of a composition comprising one or more deoxyribonucleoside monophosphates.

In a preferred embodiment, the disorder is a mitochondrial DNA depletion syndrome, and in a more preferred embodiment, the disorder is a thymidine kinase 2 (TK2) deficiency.

Other MDS disorders that can be treated with the method of the current invention include but are not limited to, deficiencies in the: DGUOK gene, encoding deoxyguanosine kinase, dGK; RRM2B gene, encoding p53R2, the p53 inducible small subunit of ribonucleotide reductase, RNR; and TYMP gene, encoding thymidine phosphorylase, TP.

In a preferred embodiment, the deoxyribonucleoside monophosphates are either deoxythymidine monophosphate (dTMP) or deoxycytidine monophosphate (dCMP) or mixtures thereof. Deoxyadenosine monophosphate (dAMP) and deoxyguanosine monophosphate (dGMP), alone or together, can be used in the method of the invention. One deoxyribonucleoside monophosphate (i.e., dCMP, dAMP, dTMP or dGMP) and mixtures of two or more deoxyribonucleoside monophosphates can be used in the method of the invention.

Preferred dosages of the deoxyribonucleoside monophosphates are between about 100 and about 1,000 mg/kg/day, more preferably between about 200 and about 800 mg/kg/day, and most preferably between about 250 and about 400 mg/kg/day. If the composition comprises a single deoxyribonucleoside monophosphate, then the dosages are of the single deoxyribonucleoside monophosphate. If the composition comprises more than one deoxyribonucleoside monophosphate, the dosages can be of each deoxyribonucleoside monophosphate or of the total deoxyribonucleoside monophosphates in the composition.

Administration of the deoxyribonucleoside monophosphates can be once daily, twice daily, three times daily, four times daily, five times daily, up to six times daily, preferably at regular intervals.

Preferred methods of administration are oral, intrathecal, intravenous, and enteral.

Administration of the deoxyribonucleoside monophosphates should begin as soon as the mitochondrial disorder is suspected and continue throughout the life of the patient. Test for the diagnosis of such disorders including TK2 deficiency are known in the art.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 2D shows histochemical analysis of muscle cytochrome c oxidase histochemical activity in $Tk2^{-/-\ 200dCMP/dTMP}$ versus $Tk2^{+200dCMP/dTMP}$. FIG. 2F is a table of mitochondrial respiratory chain activities of $Tk2^{-/-200dCMP/dTMP}$ versus $Tk2^{+200dCMP/dTMP}$ expressed in micromole/min/mg tissue and normalized to mg-protein and relative to citrate synthase (CS) (mean±SD). No statistically significant differences were detected between $Tk2^{-/-200dCMP/dTMP}$ versus $Tk2^{+200dCMP/dTMP}$ and $Tk2^{-/-400dCMP/dTMP}$ versus $Tk2^{+400dCMP/dTMP}$ samples.

Abbreviations: CS=citrate synthase; I=NADH-dehydrogenase; II=succinate dehydrogenase; III=cytochrome c reductase; IV=cytochrome c oxidase; V=ATP synthase; I+III=NADH-cytochrome c reductase; II+III=succinate cytochrome c reductase.

FIG. 3 shows the images of results of dCMP/dTMP effects on brain and spinal cord morphology. FIGS. 3A and 3B show hematoxylin and eosin stain showing numerous vacuoles in 13-day-old untreated $Tk2^{-/-}$ in brain (FIG. 3A) and spinal cord neurons (FIG. 3B). Vacuoles were rare or absent in $Tk2^{-/-200dCMP/dTMP}$ and not observed in wild-type mice.

FIG. 4 shows the complex I immunohistochemistry and complex IV histochemistry of the cerebellum. FIGS. 4A-4D show images of complex IV (COX) histochemistry of cerebellum showing deficiency in 13-day-old untreated $Tk2^{-/-}$ (FIG. 4A) in contrast to normal COX activity in $Tk2^+$ (FIG. 4B), $Tk2^{-/-200dCMP/dTMP}$ (FIG. 4C), and $Tk2^{+200dCMP/dTMP}$ (FIG. 4D) mice. FIGS. 4E-4H show COX histochemistry (FIGS. 4E and 4F) and immunostaining against COX subunit II (FIGS. 4G and 4H) of cerebellum of 29-day-old $Tk2^{-/-200dCMP/dTMP}$ (upper panels) and age-matched $Tk2^{+200dCMP/dTMP}$ mice (lower panels). FIGS. 4I and 4J show anti-complex I NDUFB8 subunit immunostaining of brain staining in 29-day-old $Tk2^{-/-200dCMP/dTMP}$ (FIG. 4I) versus $Tk2^{+200dCMP/dTMP}$ mice (FIG. 4J).

Figure 5:
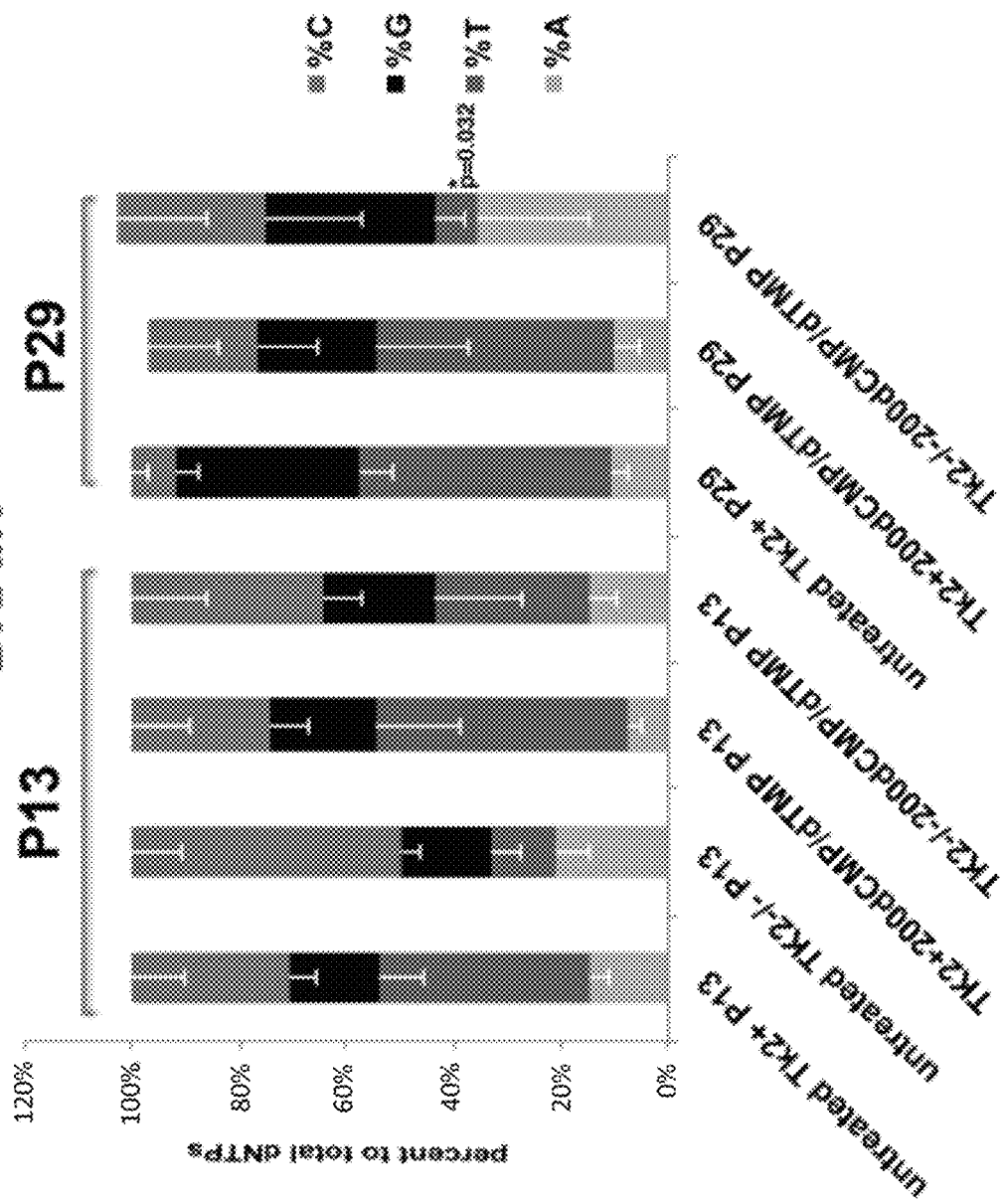
Figure 5B:
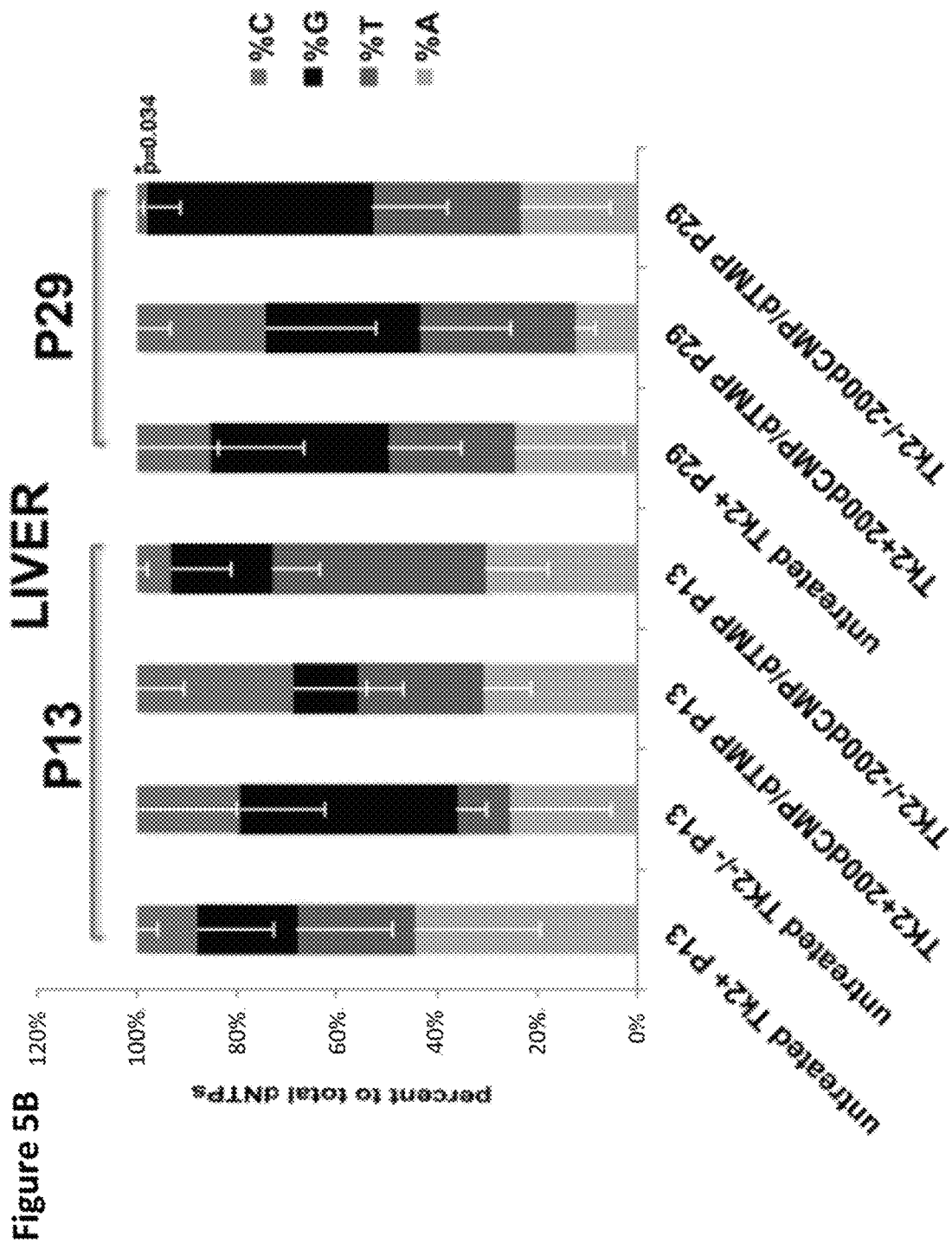

FIG. 5 shows a graphical representation of dCMP/dTMP effects on dNTP pool balance. FIG. 5A shows proportions of dNTPs (in percents) in isolated mitochondria of brain, and FIG. 5B in the liver, of 13 and 29 postnatal day mice (P13 and P29) demonstrating that levels of dTTP (red sections) were increased in treated mutant versus untreated mutant mice at P13, but were severely decreased in P29 $Tk2^{-/-200dCMP/dTMP}$ versus $Tk2^{+200dCMP/dTMP}$ (*P<0.05; ***P<0.0005; Mann-Whitney U-test).

Figure 6B:
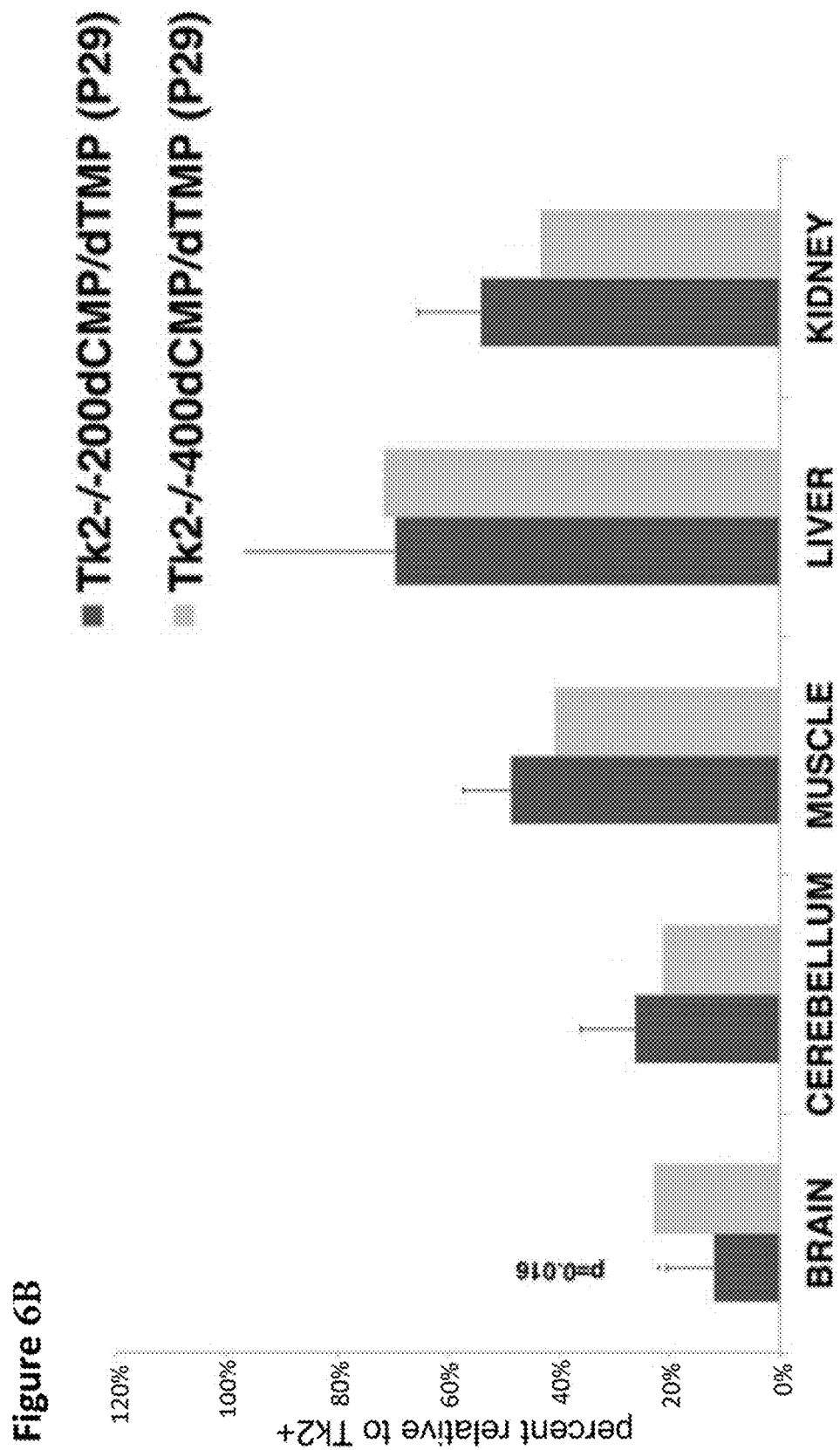

FIG. 6 shows graphs of mtDNA copy numbers in mice. FIG. 6A shows baseline mtDNA copy numbers in various tissues, and mtDNA copy numbers in the same tissues in untreated and treated mutants at P13 ($Tk2^{-/-}$ versus $Tk2^{-/-200dCMP/dTMP}$; *P<0.05; P<0.005; *P<0.0005; Mann-Whitney U-test). FIG. 6B shows mtDNA copy number in various tissues of treated mutant mice at P29 (expressed as percent of untreated $Tk2^+$ controls; mean±SD; $Tk2^{-/-200dCMP/dTMP}$ versus $Tk2^{-/-400dCMP/dTMP}$; *P<0.05; Mann-Whitney U-test) (n=5 for each group).

FIG. 7 shows the efficacy of dCMP/dTMP on brain hemisphere and cerebellum biochemistry. FIG. 7A shows a graph of CS and complex IV activity in the cerebral hemispheres of untreated $Tk2^{-/-}$ and $Tk2^{-/-200dCMP/dTMP}$ mice relative to untreated wild types (micromole/min/mg tissue normalized to mg-protein; mean±SD). FIG. 7B is a graph of complexes IV and I+III activities when referred to CS (mean±SD) in the cerebral hemispheres of untreated $Tk2^{-/-}$ and $Tk2^{-/-200dCMP/dTMP}$ mice relative to untreated wild types (micromole/min/mg tissue normalized to mg-protein; mean±SD). FIG. 7C is a graph of the activities of mitochondrial RC referred to CS (expressed as percent of $Tk2+$) in the cerebellum of mutant mice at ages 13 and 29 days, treated and untreated. FIG. 7D is a western blot of OXPHOSprotein (MitoProfile® Total OXPHOS Rodent WB Antibody Cocktail, MitoSciences®) in brain 13-day-old untreated $Tk2^{-/-}$, 13- and 29-day-old $Tk2^{-/-200dCMP/dTMP}$ mice and FIG. 7E in the cerebellum of 13-day-old untreated $Tk2^{-/-}$, 13- and 29-day-old $Tk2^{-/-200dCMP/dTMP}$ mice, and $Tk2^{-/-400dCMP/dTMP}$ (expressed as percentages relative to $Tk2+$). FIGS. 7F, 7G, and 7H are graphical quantitation of western blot bands.

Figure 7C:
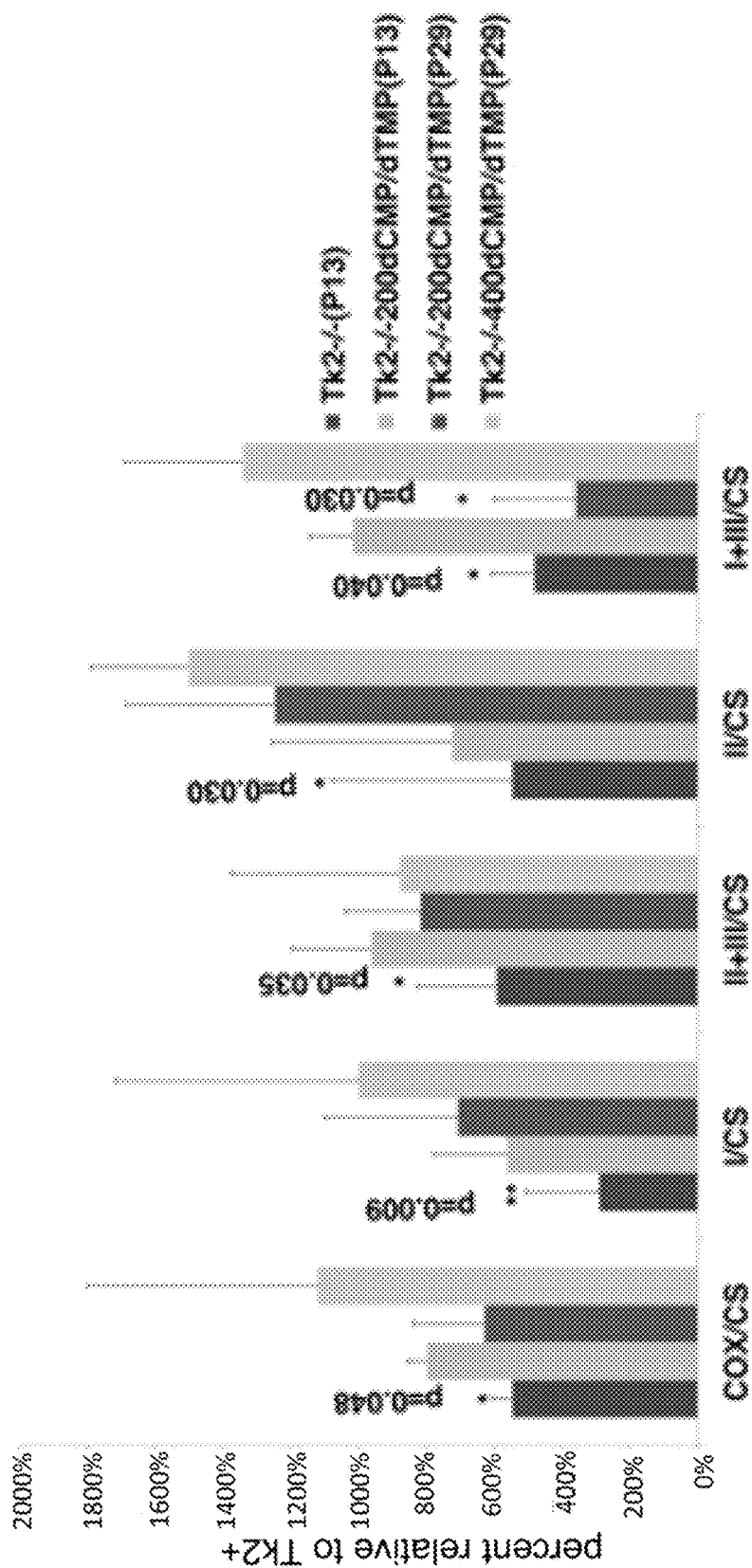
Figure 7E:
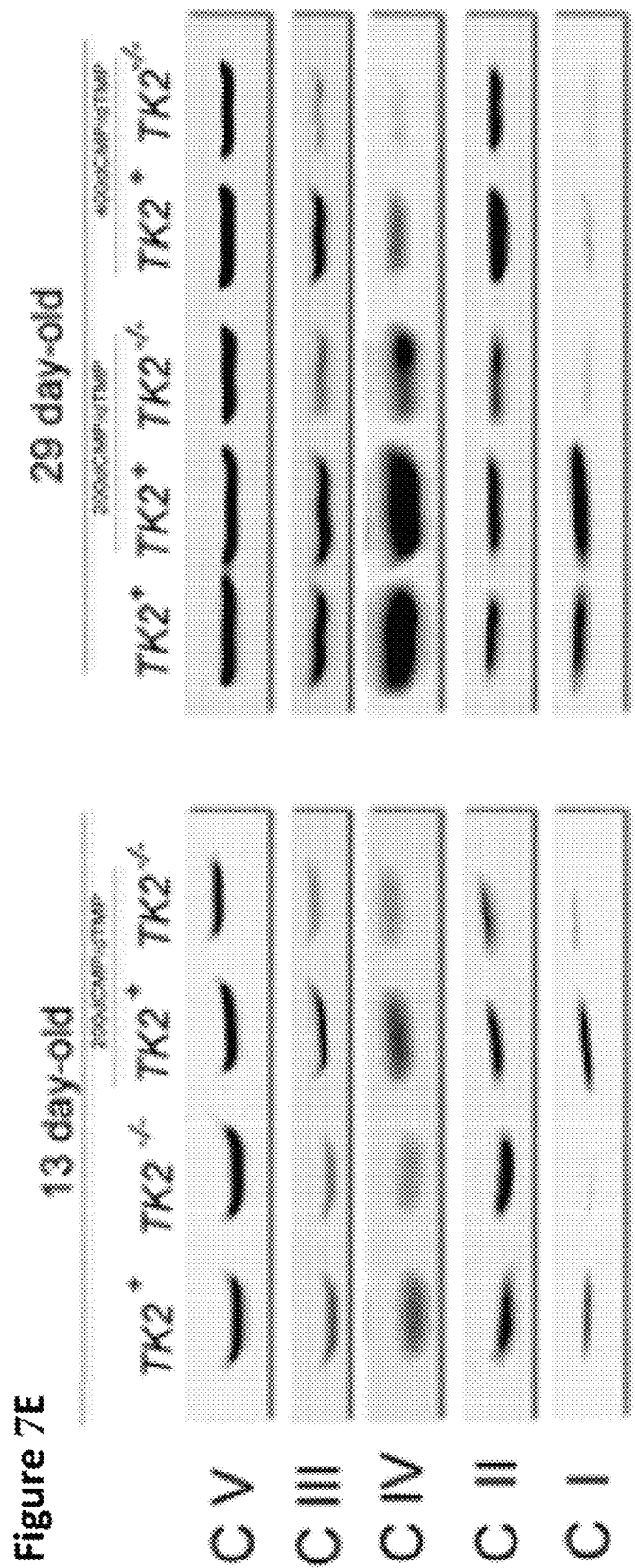
Figure 7F:
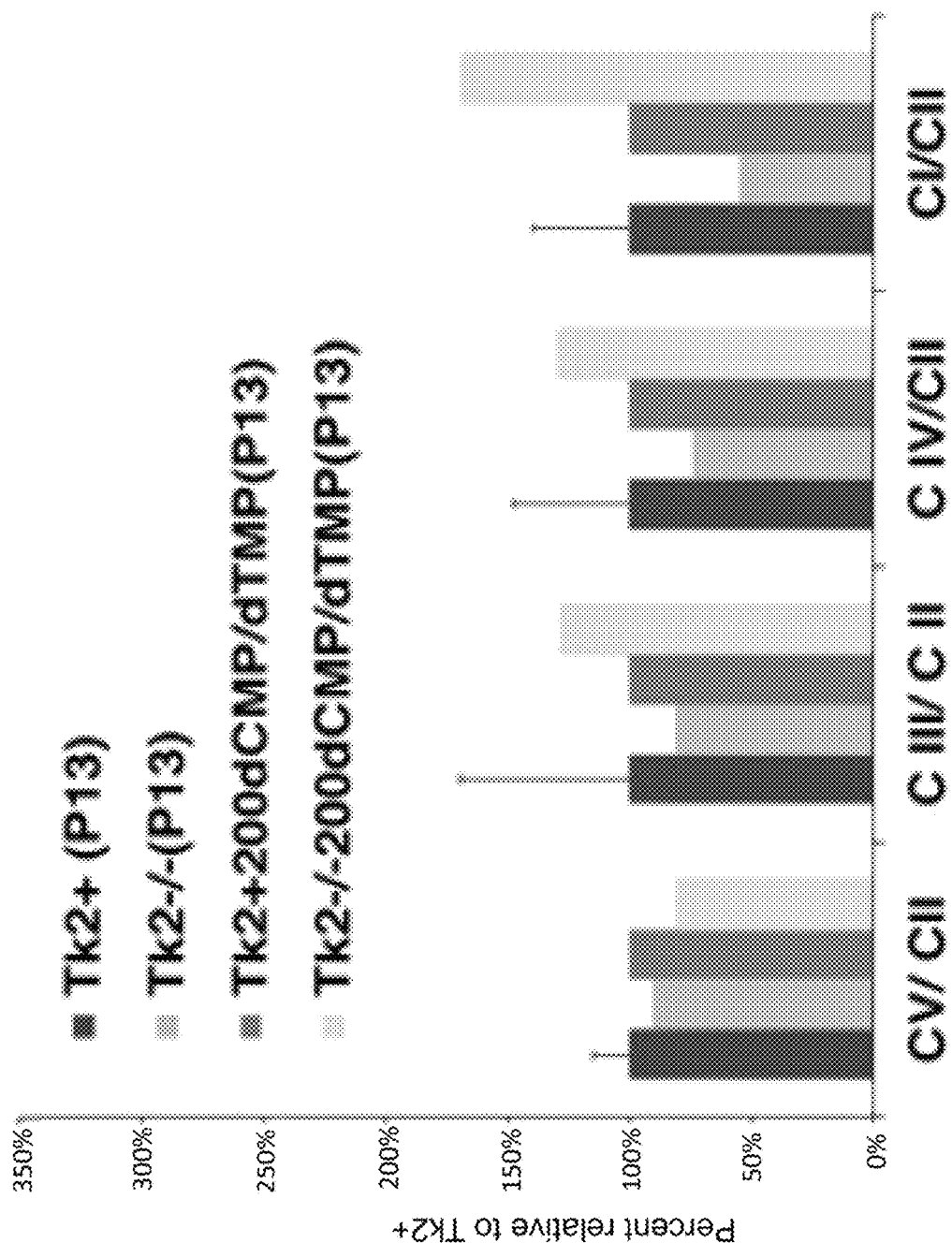
Figure 7G:
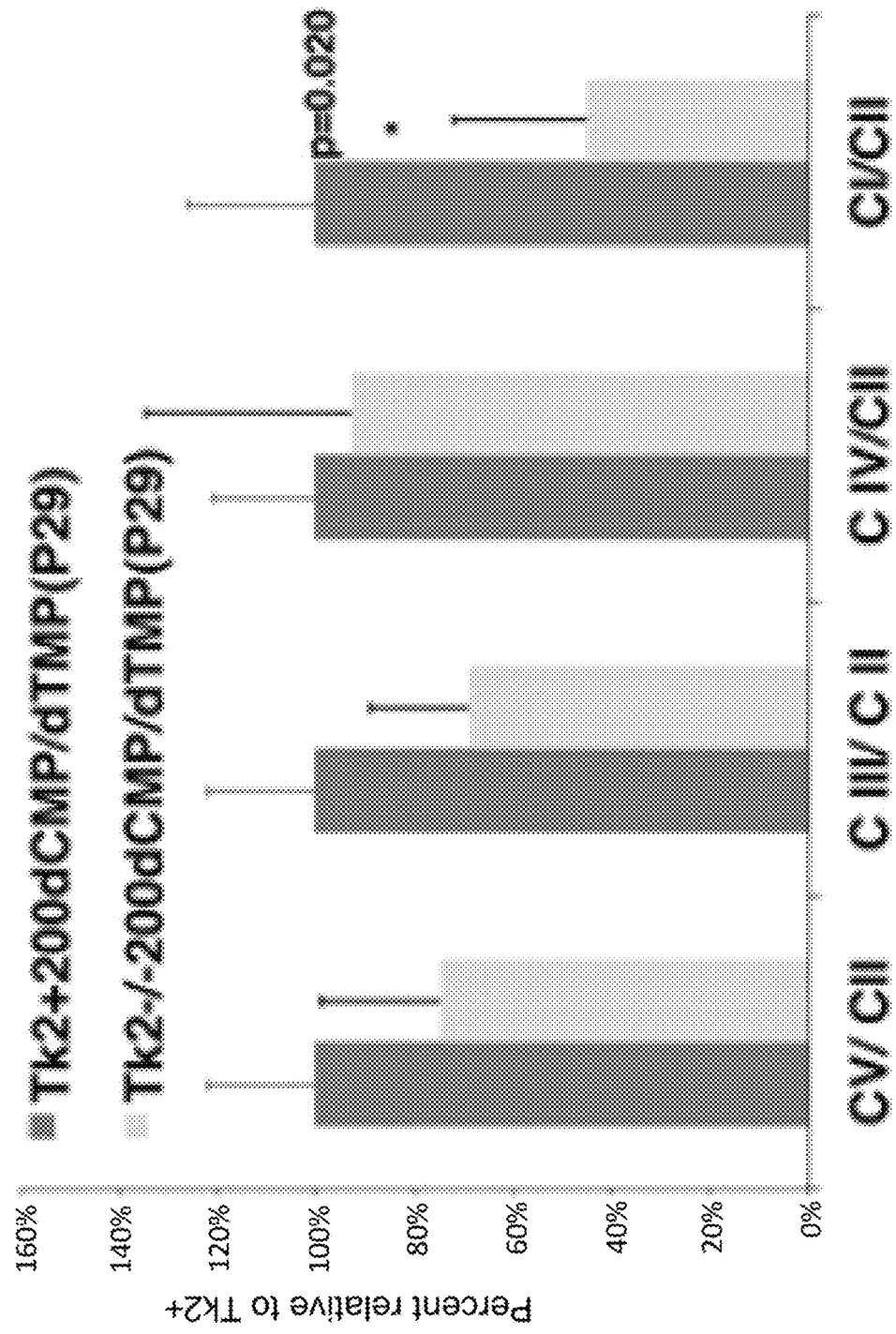

Statistical analyses were performed using $Tk2^{-/-}$ versus $Tk2^{-/-200dCMP/dTMP}$ with P13 cerebral samples (FIG. 7F); $Tk2^{-/-200dCMP/dTMP}$ versus $Tk2^{+200dCMP/dTMP}$ with P29 cerebral samples (FIG. 7G); $Tk2^{-/-}$ versus $Tk2^{-/-200dCMP/dTMP}$ with P13 cerebellar samples (FIG. 7H); and $Tk2^{-/-200dCMP/dTMP}$ versus $Tk2^{-/-400dCMP/dTMP}$ with P29 cerebellar samples (H). *P<0.05; **P<0.005; Mann-Whitney U-test and Unpaired t-test with Welch's correction).

Abbreviations: CS=citrate synthase; IV=cytochrome c oxidase (COX); I+III=NADH-cytochrome c reductase; I=NADH-dehydrogenase; II=succinate dehydrogenase; III=cytochrome c reductase; V=ATP synthase; P=postnatal day.

FIG. 8 is graphs showing the metabolism of dCMP/dTMP. FIGS. 8A-8C are graphs showing the levels of deoxyuridine and deoxythymidine in liver (FIG. 8A), brain (FIG. 8B), and muscle tissues (FIG. 8C) in untreated mutant mice and treated mutant mice at P13 and P29. Deoxynucleoside levels are expressed as percentages relative to age-matched untreated wild-type controls (mean±SD) ($Tk2^{-/-200dCMP/dTMP}$, $Tk2^{+200dCMP/dTMP}$, $Tk2^{-/-400dCMP/dTMP}$, and $Tk2^{+400dCMP/dTMP}$ versus untreated $Tk2+$; *P<0.05;**P<0.005; Unpaired t-test with Welch's correction; n>3 mice for each group). FIG. 8D is a graph showing thymidine phosphorylase (TP) activity in small intestine of treated and untreated Tk2 mice at age 29 days relative to 13 days. Data expressed as nmol/h/mg-proteins (mean±SD). FIGS. 8E and 8F are graphs of Tk1 and Tk2 activities in brain (FIG. 8E) and muscle tissues (FIG. 8F) of treated and untreated mice showing increased Tk1 activity in treated mice. Data expressed in pmol/min/mg-proteins (mean±SD) ($Tk2^{+/+}$ versus $Tk2^{+/+200dCMP/dTMP}$; $Tk2^{+/-}$ versus $Tk2^{+/-200dCMP/dTMP}$; $Tk2^{-/-}$ versus $Tk2^{-/-200dCMP/dTMP}$; *P<0.05; Unpaired t-test with Welch's correction; n>3 mice for each group). P=p-value.

DETAILED DESCRIPTION OF THE INVENTION

The current invention is based upon the surprising discovery that mitochondrial DNA depletion syndromes, including TK2 deficiency, can be treated with a molecular bypass approach. As shown by the results herein, the administration of deoxyribonucleoside monophosphates greatly improved the condition in both a mouse model of TK2 deficiency and human patients with TK2 deficiency.

Definitions

The terms used in this specification generally have their ordinary meanings in the art, within the context of this invention and the specific context where each term is used.

Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means mammals. Mammals include canines, felines, rodents, bovine, equines, porcines, ovines, and primates. Thus, the invention can be used in veterinary medicine, e.g., to treat companion animals, farm animals, laboratory animals in zoological parks, and animals in the wild. The invention is particularly desirable for human medical applications The term "patient" as used in this application means a human subject. In some embodiments of the present invention, the "patient" is known or suspected of having mitochondrial disease, mitochondrial DNA depletion syndrome, or TK2 deficiency.

The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject.

The terms "treat", "treatment", and the like refer to a means to slow down, relieve, ameliorate or alleviate at least one of the symptoms of the disease or disorder, or reverse the disease or disorder after its onset.

The terms "prevent", "prevention", and the like refer to acting prior to overt disease or disorder onset, to prevent the disease or disorder from developing or minimize the extent of the disease or disorder, or slow its course of development.

The term "in need thereof" would be a subject known or suspected of having or being at risk of having mitochondrial disease, mitochondrial DNA depletion syndrome, or TK2 deficiency.

The term "agent" as used herein means a substance that produces or is capable of producing an effect and would include, but is not limited to, chemicals, pharmaceuticals, biologics, small organic molecules, antibodies, nucleic acids, peptides, and proteins.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Deoxypyrimidine Monophosphate Bypass Therapy Mouse Model of TK2 Deficiency

Attempts to study the pathogenesis and test therapies for TK2 deficiency using cultured fibroblasts from patients had proved unsuccessful because the replicating cells failed to manifest mtDNA depletion. Thus, to elucidate the molecular pathogenesis of TK2 deficiency, a homozygous Tk2 H126N knock-in mutant (Tk2$^{-/-}$) mouse that manifests a phenotype strikingly similar to the human infantile encephalomyopathy was generated and previously reported by the inventors (Akman, et al. 2008) (Example 1).

Figures 1, 1A:
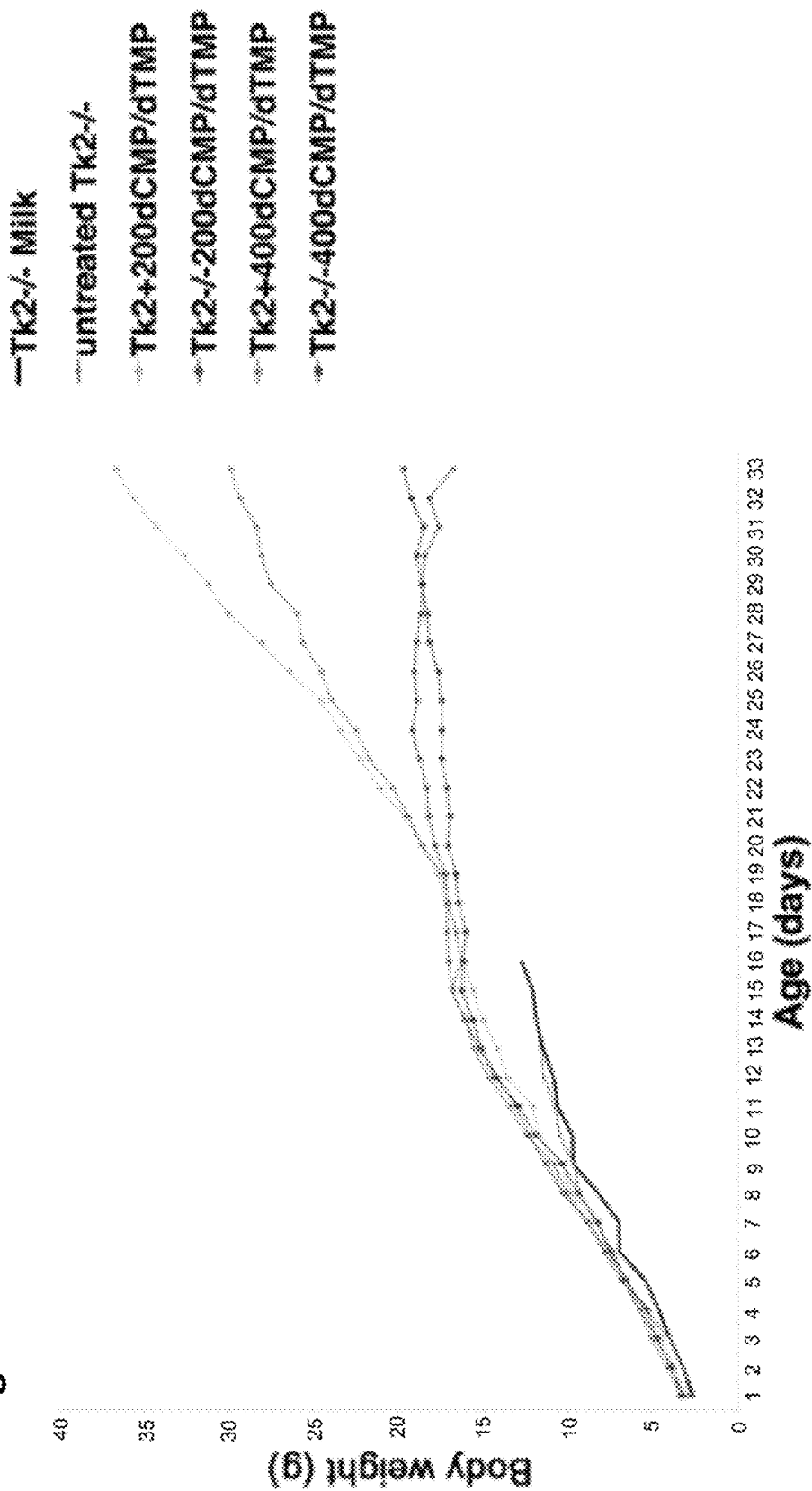
FIG. 1 shows the efficacy of dCMP/dTMP on clinical phenotype in treated $Tk2^{-/-}$ mice.
FIG. 1A is a graph of body weight versus age in days, and FIG. 1B of survival of untreated and treated $Tk2^{-/-}$ mice (n=7 for each group) ($Tk2^{-/-}$ versus $Tk2^{-/-200dCMP/dTMP}$, $P<0.005$; $Tk2^{-/-}$ versus $Tk2^{-/-400dCMP/dTMP}$, $P<0.005$; Gehan-Breslow-Wilcoxon test).
Figures 2, 2A:
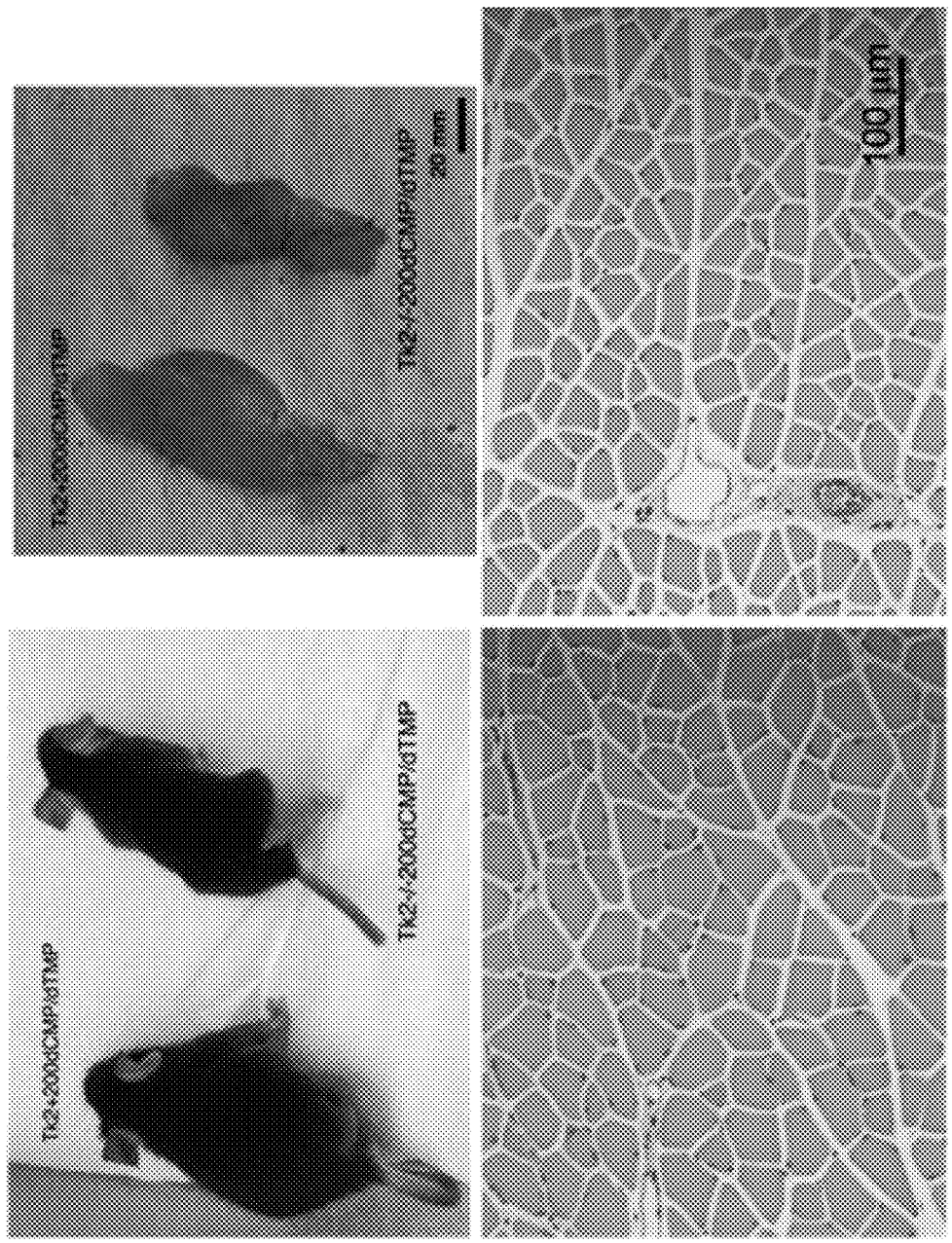
FIG. 2 shows the neuromuscular phenotype in 29-day old treated mice.
FIG. 2A shows body size, quadriceps muscle size, and myofiber diameters in $Tk2^{-/-200dCMP/dTMP}$ (right panels) versus $Tk2^{+200dCMP/dTMP}$.
Figure 2B:
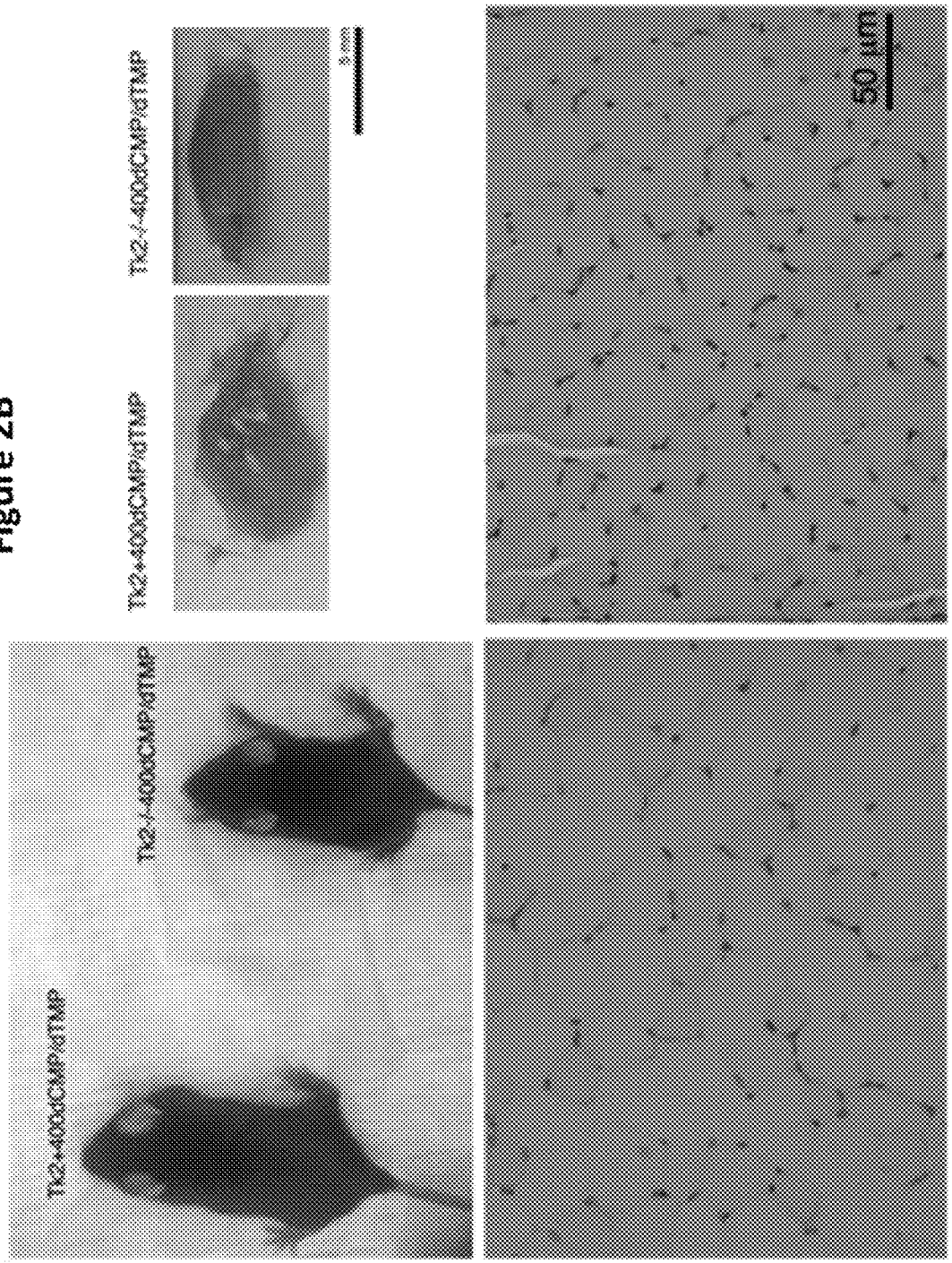
FIGS. 2B and 2C show body size, quadriceps muscle size, and myofiber diameters in $Tk2^{-/-400dCMP/dTMP}$ versus $Tk2^{+400dCMP/dTMP}$.
Figure 2C:
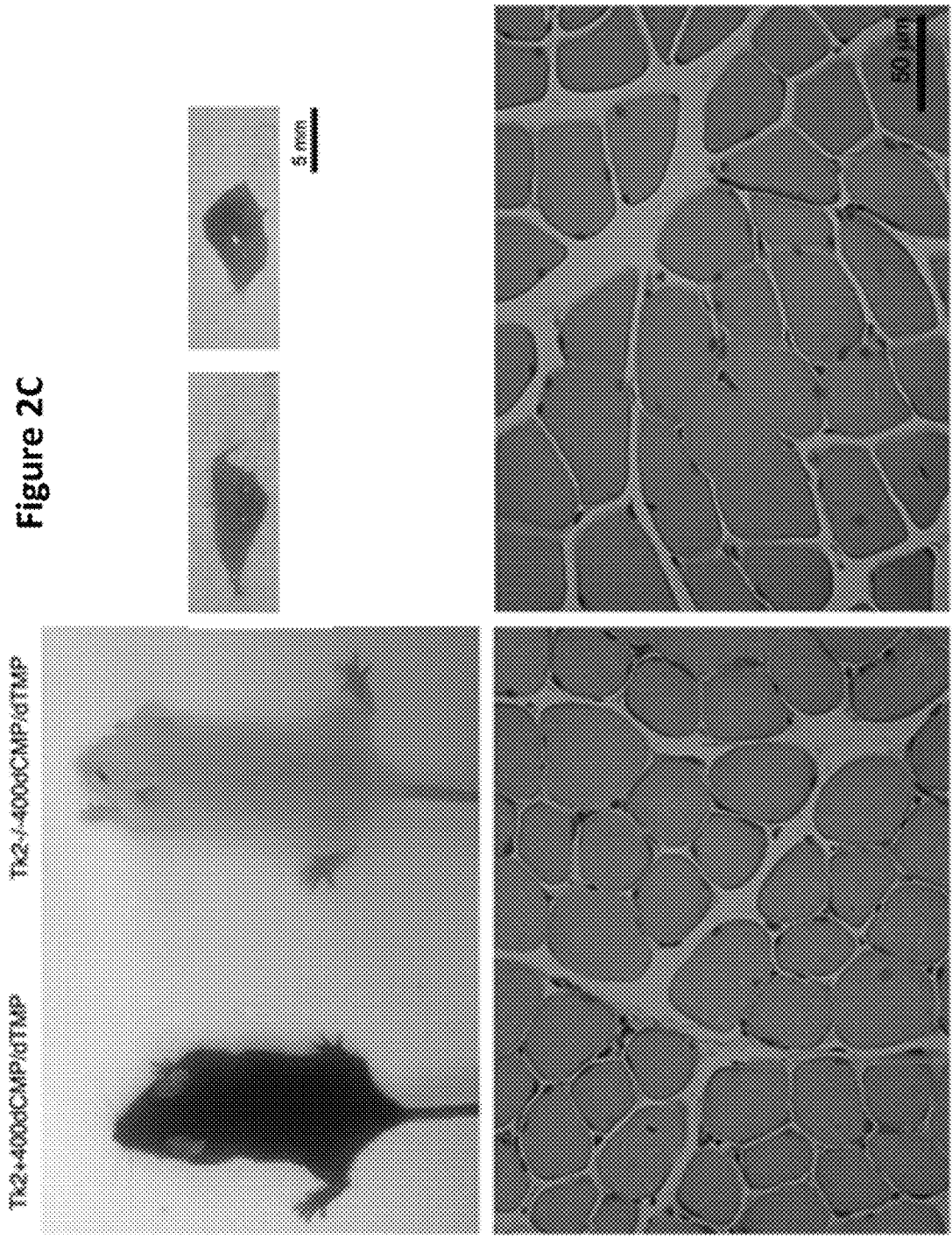

Based upon the understanding of the pathogenesis of Tk2 deficiency, a rationale therapeutic strategy to bypass the enzymatic defect with oral dCMP and dTMP supplementation was designed and implemented (Example 1). Surprisingly, the results herein demonstrate that the molecular bypass therapy with orally administered dCMP and dTMP delayed disease onset, ameliorated the abnormal phenotype and extended the lifespan of Tk2$^{-/-}$ mice by 2-3 fold. Additionally, no adverse side effects, including malignancies, were observed (Example 2; FIGS. 1 and 2).

Oral dTMP/dCMP crossed biological barriers including the blood-brain barrier (BBB) because treatment increased dTTP in brain and liver in 13-day-old Tk2$^{-/-}$ mice and augmented levels of mtDNA, restoring the mitochondrial RC activities and protein defects in brain, heart, muscle, liver, and kidney of 13- and 29-day-old mutant mice (Examples 4 and 5; FIGS. 5 and 6). Of particular relevance is the observation that treatment caused marked improvements of mtDNA levels and biochemical defects in muscle, because muscle is the most affected tissue in TK2 deficient patients.

Previous studies have found that wild-type Tk2 (mitochondrial) activity is constant in the second week of life while cytosolic Tk1 activity decreases significantly between postnatal day 8 and 13. The down-regulation of Tk1 activity unmasks Tk2 deficiency in Tk2$^{-/-}$ mice and correlates with the onset of mtDNA depletion in brain and heart (Dorado, et al. 2011). The results herein demonstrated that oral dCMP and dTMP delayed the reduction in Tk1 activity (Example 6; FIGS. 8E and 8F). Thus, in addition to providing substrates for dNTP synthesis, dCMP/dTMP supplementation in Tk2$^{-/-}$ mice also enhanced the compensatory Tk1 activity.

The data in mice shown herein proves that deoxypyrimidine supplementation for Tk2 deficiency is the first effective and safe in vivo treatment option for patients affected by Tk2 mutations. See Garone, et al. 2014, herein incorporated by reference in its entirety. Based upon this data, the administration of deoxyribonucleoside monophosphates was hypothesized to improve the conditions of human patients with TK2 deficiency, even though mouse models have revealed important differences in dNTP homeostasis between mice and humans.

Furthermore, this approach is applicable to individuals with other mitochondrial disorders due to nucleotide pools unbalance.

Patients Benefiting from the Administration of Deoxyribonucleoside Monophosphates The present invention includes the administration of at least one deoxyribonucleoside monophosphate to a patient in need thereof. In one embodiment, the present invention includes the administration of at least one deoxypyrimidine monophosphate. In a further embodiment, the dexypyrimidine monophosphate is chosen from dCMP, dTMP and mixtures thereof. In yet another embodiment, the present invention includes the administration of at least one deoxypurine monophosphate. In a further embodiment, the deoxypurine monophosphate is chosen from dAMP, dGMP, and mixtures thereof.

As shown in Examples 7-10, the administration of dTMP and dCMP greatly improved the symptoms of TK2 deficiency in patients, especially with regard to muscular-related symptoms. Thus, patients who would benefit from the deoxypyrimidine monophosphate bypass therapy would be those diagnosed with TK2 deficiency. In these patients, at least one deoxypyrimidine monophosphate, dCMP or dTMP, or mixtures thereof would be administered.

A parallel defect of deoxyguanosine kinase (dGK), due to autosomal recessive mutations in DGUOK with deficiencies in dGMP and dAMP, causes mtDNA depletion typically manifesting as early childhood-onset hepatocerebral disease (Mandel et al., 2001). These patients would benefit from the administration of at least one deoxypurine monophosphates, dGMP or dAMP, or mixtures thereof.

Other forms of MDS as well as other disorders related to unbalanced nucleotide pools can be treated by the administration of specific deoxyribonucleoside monophosphate, i.e., dAMP, dGMP, dCMP, or dTMP, or mixtures thereof. These disorders would include but are not limited to deficiencies related to RRM2B (encoding p53R2, the p53-inducible small subunit of ribonucleotide reductase, RNR) and mutations in TYMP (encoding thymidine phosphorylase, TP) which cause mitochondrial neurogastrointestinal encephalomyopathy (MNGIE).

Additionally, as the mechanisms of other forms of MDS and other disorders become elucidated, the proper deoxyribonucleoside monophosphate(s) for treatment can be determined by the skilled practitioner.

Patients that exhibit the phenotype discussed above for TK2 deficiency including the most typical presentation of progressive muscle disease characterized by generalized hypotonia, proximal muscle weakness, loss of previously acquired motor skills, poor feeding, and respiratory difficulties, can be tested to definitively diagnose the disease.

If the clinical presentation is highly suspicious for mtDNA depletion syndrome, molecular genetic testing using a panel of genes known to cause mtDNA depletion syndrome should be performed (Chanprasert, et al. 2012). The TK2 gene is the only gene in which mutations are known to cause TK2-related mitochondrial DNA depletion syndrome. This testing can include a sequence analysis of the entire coding and exon/intron junction regions of TK2 for sequence variants and deletion/duplication. If compound heterozygous or homozygous deleterious mutations are identified in the sequence analysis, the diagnosis of TK2 deficiency is confirmed, and thus, the subject would benefit from the deoxypyrimidine monophosphate therapy. If sequence analysis does not identify two compound heterozygous or homozygous deleterious mutations, deletion/duplication analysis should be considered to determine and/or confirm a TK2 deficiency diagnosis.

Further tests to determine and/or confirm a TK2 deficiency diagnosis may include testing serum creatine kinase (CK) concentration, electromyography, histopathology on skeletal muscle, mitochondrial DNA (mtDNA) content (copy number), and electron transport chain (ETC) activity in skeletal muscle. If one or more of the following is found in these tests, the TK2 deficiency is determined and/or confirmed. Elevated CK concentration as compared to healty controls can indicate TK2 deficiency. A skeletal muscle biopsy can be performed, and then a mtDNA content analysis in skeletal muscle performed. If the skeletal muscle biopsy shows prominent variance in fiber size, variable sarcoplasmic vacuoles, variable increased connective tissue, and ragged red fibers as well as increased succinate dehydrogenase (SDH) activity and low to absent cytochrome c oxidase (COX) activity, and mtDNA copy number is severely reduced (typically less than 20% of age- and tissue-matched healthy controls), a diagnosis of TK2 deficiency can be determined and/or confirmed (Chanprasert, et al. 2012).

Additionally, TK2 deficiency is inherited in an autosomal recessive manner. Thus, a sibling of an affected patient can be tested as early as possible after birth to diagnose the disease.

In all of these examples, deoxypyrimidine monophosphate bypass therapy should be started as soon as possible after a diagnosis of TK2 deficiency.

Pharmaceutical Compositions, Methods of Administration, and Dosing

The present invention encompasses the administration of deoxyribonucleoside monophosphates. Most preferred methods of administration are oral, intrathecal and parental including intravenous. The deoxyribonucleoside monophosphates must be in the appropriate form for administration of choice.

The preferred form of the administration of the deoxyribonucleoside monophosphates is in the form of disodium salts of the deoxyribonucleoside monophosphates. These disodium salts (dTMP $Na_2$, dCMP $Na_2$ salts) are easily dissolved in liquid (such as water, formula or milk) whereas the free acid form does not readily dissolve in liquid. Once administered, the deoxyribonucleoside monophosphates salts convert to the free acid form. By way of example, for some of the oral administration to human patients, 2000 mg each of dTMP $Na_2$ and dCMP $Na_2$ were dissolved in 25 ml of water.

Such compositions for administration may comprise a therapeutically effective amount of the deoxyribonucleoside monophosphates and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans.

"Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Oral administration is a preferred method of administration. The deoxyribonucleoside monophosphates can be added to any form of liquid a patient would consume including but not limited to, milk, both cow's and human breast, infant formula, and water.

Additionally, pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

In order to overcome issue of the deoxynucleoside monophosphates crossing the blood/brain barrier, intrathecal administration is a further preferred form of administration of deoxyribonucleoside monophosphates (Galbiati, et al. 2006; Gotz, et al. 2008). Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

A further preferred form of administration is parenteral including intravenous administration. Pharmaceutical compositions adapted for parenteral administration, including intravenous administration, include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Additionally, since some patients may be receiving enteral nutrition by the time the deoxyribonucleoside monophosphate treatment begins, the dNMPs can be administered through a gastronomy feeding tube or other enteral nutrition means.

Further methods of administration include mucosal, such as nasal, sublingual, vaginal, buccal, or rectal; or transdermal administration to a subject.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for transdermal administration may be provided as discrete patches intended to remain in intimate contact with the epidermis of the recipient over a prolonged period of time.

Selection of a therapeutically effective dose will be determined by the skilled artisan considering several factors, which will be known to one of ordinary skill in the art. Such factors include the particular form of the deoxyribonucleoside monophosphate, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

A preferred dose ranges from about 100 mg/kg/day to about 1,000 mg/kg/day. A further preferred dose ranges from about 200 mg/kg/day to about 800 mg/kg/day. A further preferred dose ranges from about 250 mg/kg/day to about 400 mg/kg/day. These dosage amounts are of individual deoxyribonucleoside monophosphates or of a composition with a mixture of more than one deoxyribonucleoside monophosphates, e.g., dTMP and dCMP. For example, a dose can comprise 400 mg/kg/day of dTMP alone. In a further example, a dose can comprise a mixture of 200 mg/kg/day of dTMP and 200 mg/kg/day of dCMP. In a further example, a dose can comprise 400 mg/kg/day of a mixture of dTMP and dCMP.

Administration of the deoxyribonucleoside monophosphates can be once a day, twice a day, three times a day, four times a day, five times a day, up to six times a day, preferably at regular intervals. For example, when the deoxyribonucleoside monophosphates are administered four times daily, doses would be at 8:00 AM, 12:00 PM, 4:00 PM, and 8:00 PM.

As shown in the Examples, doses can be adjusted to optimize the effects in the subject. For example, the deoxyribonucleoside monophosphates can be administered at 100 mg/kg/day to start, and then increased over time to 200 mg/kg/day, to 400 mg/kg/day, to 800 mg/kg/day, up to 1000 mg/kg/day, depending upon the subject's response.

A subject can be monitored for improvement of their condition prior to increasing the dosage. Also as shown in the Examples, a subject's response to the therapeutic administration of the deoxyribonucleoside monophosphates can be monitored by observing a subject's muscle strength and control, and mobility as well as changes in height and weight. If one or more of these parameters increase after the administration, the treatment can be continued. If one or more of these parameters stays the same or decreases, the dosage of the deoxyribonucleoside monophosphates can be increased.

The deoxyribonucleoside monophosphates can also be co-administered with other agents. Such agents would include therapeutic agents for treating the symptoms of the particular form of MDS. In particular, for TK2 deficiency, the dTMP and dCMP can be co-administered with an inhibitor of thymidine phosphorylase (e.g. tipiracil) or an inhibitor of cytidine deaminase (e.g. tetrahydrouridine [THU]) (see Example 6). Such inhibitors are known and used in the treatment of some cancers.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods for Examples 2-6

Mouse Model of TK2 Deficiency

A homozygous Tk2 H126N knock-in mutant ($Tk2^{-/-}$) mouse that manifests a phenotype strikingly similar to the human infantile encephalomyopathy has been previously reported (Akman, et al. 2008). Between postnatal day 10 and 13, $Tk2^{-/-}$ mice rapidly develop fatal encephalomyopathy characterized by decreased ambulation, unstable gait, coarse tremor, growth retardation, and rapid progression to early death at age 14 to 16 days. Molecular and biochemical analyses of the mouse model demonstrated that the pathogenesis of the disease is due to loss of enzyme activity and ensuing dNTP pool imbalances with decreased dTTP levels in brain and both dTTP and dCTP levels in liver, which, in turn, produces mtDNA depletion and defects of respiratory chain enzymes containing mtDNA-encoded subunits, most prominently in the brain and spinal cord (Dorado, et al. 2011).

All experiments were performed according to a protocol approved by the Institutional Animal Care and Use Committee of the Columbia University Medical Center, and were consistent with the National Institutes of Health Guide for the Care and Use of Laboratory Animals. Mice were housed and bred according to international standard conditions, with a 12-hour light, 12-hour dark cycle, and sacrificed at 4, 13, and 29 days of age.

Organs (brain, spinal cord, liver, heart, kidney, quadriceps muscle, lung, and gastrointestinal tract) were removed and either frozen in the liquid phase of isopentane, pre-cooled near its freezing point (−160° C.) with dry ice or fixed in 10% neutral buffered formalin and embedded in paraffin using standard procedures. Paraffin embedded tissue were then stained with hematoxylin and eosin (H&E) for morphological study or processed for immunostaining studies with GFAP, COX I, or complex I subunit as detailed below. All the experiments were performed in at least 3 mice per group. Both heterozygous and homozygous wild type mice were considered as control group ($Tk2^+$) since no clinical and biochemical difference were previously described (Akman et al, 2008; Dorado et al, 2011).

Treatment Administration and Experimental Plan

Deoxycytidine monophosphate (dCMP) and deoxythymidine monophosphate (dTMP) (Hongene Biotech, Inc.) were administered in 50 al of Esbilac milk formula for small pets (Pet-Ag) by daily oral gavage to Tk2 H126N knock-in mice ($Tk2^{-/-}$) and aged-matched control wild-type ($Tk2^+$) using 2 doses, 200 mg/kg/day and 400 mg/kg/day, from post-natal day 4 to 29 days. At age 29 days, mice were separated from the mother and the treatment was continued by administration of dCMP and dTMP in drinking water using equimolar doses, respectively of 1.6 mM and 3.2 mM. A negative control group of untreated Tk2 mutant and control wild-type mice were weighted and observed closely for comparison.

Phenotype Assessment

To define the degree of safety and efficacy of dTMP/dCMP, survival time, age-at-onset of disease, type and severity of symptoms, occurrence of side effects, and proportion of treatment termination due to adverse events, in treated and untreated Tk2 mice were compared. General behavior, survival time, and body weights of the mice were assessed daily beginning at postnatal day 4. Videotaping and open-field test with an Opto-Varimetrix-3 sensor system (Columbus Instruments) were performed at 13 and 29 days by counting horizontal and vertical movements, recording ambulatory and resting time, and measuring the total distance traveled in 10 minutes.

Brain Histology

Brain and spinal cord samples from 13- to 29-day-old mice were fixed with 10% neutral-buffered formalin and embedded in paraffin using standard procedures. Cerebellum, brainstem, hippocampus, cerebral cortex, and cervical, thoracic and lumbar tracts of the spinal cord were analyzed.

Sections (5 µm thick) were stained with H&E and luxol fast blue to analyze the overall structure of the tissue. Immunostaining with antibodies against GFAP, complex I (NDUFB6), or COX subunit 2 was also performed. Briefly, paraffin-embedded brain and spinal cord slides were deparaffinized, rehydrated, and rinsed in phosphate-buffered saline solution (PBS). To block endogenous peroxidase activity, sections were incubated with 3% hydrogen peroxide in methanol. Slides were then placed in 0.1 M sodium citrate buffer (pH 6.0) and heated in a microwave oven for 15 minutes, for antigen retrieval. Slides were incubated with mouse anti-GFAP antibody (1:100) (Novocastra. NCL-GFAP-GA5) or mouse monoclonal antibody anti-complex I 17 kDa (NDUFB6) subunit (1:100) (A21359; Molecular Probes) or mouse monoclonal antibody anti-COX subunit 2 (1:100) (clone COX 229, A6404; Molecular Probes) overnight at 4° C. Sections were subsequently rinsed in PBS and incubated with anti-mouse M.O.M. Peroxidase kit, 1:200 dilution for 60 minutes at room temperature. Immunoreactivity was detected by avidin-biotin complex (ABC) with DAB substrate (Vector Laboratories, Burlingame, Calif., USA). Slides were examined by light microscopy using an Olympus BX51 microscope, and images were captured with a QImaging Retiga EXi digital camera, using QCapture software version 2.68.6.

dNTP Pool by Polymerase Extension Assay

Tissues were homogenized on ice in 10 volumes (w/v) of cold MTSE buffer (210 mM mannitol, 70 mM sucrose, 10 mM Tris-HCl pH 7.5, 0.2 mM EGTA, 0.5% BSA) and centrifuged at 1,000 g for 5 minutes at 4° C., followed by three centrifugations at 13,000 g for 2 minutes at 4° C. Supernatant was precipitated with 60% methanol for the mitochondrial fraction and 100% methanol for the cytosolic fraction, kept 2 hours at −80° C., boiled 3 minutes, stored at −80° C. (from 1 hour to overnight), and centrifuged at 20,800 g for 10 minutes at 4° C. Supernatants were evaporated until dry, and pellet was resuspended in 65 µl of water and stored at −80° C. until analyzed.

To minimize ribonucleotide interference, total dNTP pools were determined as previously reported (Ferraro, et al. 2010; Marti, et al. 2012). Briefly, 20 µl volume reactions was generated by mixing 5 µl of sample or standard with 15 µl of reaction buffer (0.025 U/ml ThermoSequenase DNA polymerase (GE Healthcare, Piscataway, N.J., USA) or Taq polymerase (Life Technologies, NY, USA), 0.75 µM $^3$H-dTTP or $^3$H-dATP (Moravek Biochemicals), 0.25 µM specific oligonucleotide, 40 mM Tris-HCl, pH 7.5, 10 mM $MgCl_2$, 5 mM DTT). After 60 minutes at 48° C., 18 ml of reaction were spotted on Whatman DE81 filters, air dried, and washed three times for 10 minutes with 5% $Na_2HPO_4$, once in distilled water and once in absolute ethanol. The retained radioactivity was determined by scintillation counting.

Nucleosides Measurement by HPLC

Deoxythymidine (dT), deoxyuridine (dU), uracil (U), and thymine (T) levels were assessed by a gradient-elution HPLC method as described previously (Lopez, et al. 2009; Marti, et al. 2012), with minor modifications. Briefly, deproteinized samples were injected into an Alliance HPLC system (Waters Corporation) with an Alltima C18NUC reversed-phase column (Alltech) at a constant flow rate of 1.5 ml/min (except where indicated) using three buffers: eluent A (20 mM potassium phosphate, pH 5.6), eluent B (water), and eluent C (methanol). Samples were eluted over 60 minutes with a gradient as follows: 0-5 min, 100% eluent A; 5-25 min, 100-71% eluent A, 29% eluent B; 25-26 min, 0-100% eluent C; 26-30 min, 100% eluent C; 30-31 min, 0-100% eluent B; 31-35 min, 100% eluent B (1.5-2 ml/min); 35-45 min, 100% eluent B (2 ml/min); 45-46 min, 100% eluent B (2-1.5 ml/min); 46-47 min, 0-100% eluent C; 47-50 min, 100% eluent C; 50-51 min, 0-100% eluent A; and 51-60 min, 100% eluent A.

Absorbance of the elutes was monitored at 267 nm, and dThd and dUrd peaks were quantified by comparing their peak areas with a calibration curve obtained with aqueous standards. For definitive identification of dT, dU, U, and T peaks for each sample, a second aliquot treated with excess of purified E. coli TP (Sigma) was used to specifically eliminate dT and dU. The detection limit of this method is 0.05 mmol/l for all nucleosides.

RT-qPCR: Mitochondrial DNA Quantification

Real-time PCR was performed with the primers and probes for murine COX I gene (mtDNA) and mouse glyceraldehyde-3-phosphate dehydrogenase (GAPDH, nDNA) (Applied Biosystems, Invitrogen, Foster City, Calif., USA) as described using standard curve quantification, in an ABI PRISM 7,000 Sequence Detection System (Applied Biosystems) (Dorado, et al. 2011). MtDNA values were normalized to nDNA values and expressed as percent relative to wild type (100%).

Mitochondrial Respiratory Chain Protein Levels

Thirty micrograms of whole brain cerebrum or cerebellum extracts was electrophoresed in an SDS-12% PAGE gel, transferred to Immun-Blot™ PVDF membranes (Bio-Rad, Hercules, Calif., USA) and probed with MitoProfile® Total OXPHOS Rodent WB Antibody Cocktail of antibodies (MitoSciences, Eugene, Oreg., USA). Protein-antibody interaction was detected with peroxidase-conjugated mouse anti-mouse IgG antibody (Sigma-Aldrich, St Louis, Mo., USA), using Amersham™ ECL Plus western blotting detection system (GE Healthcare Life Sciences, UK). Quantification of proteins was carried out using NIH ImageJ 1.37V software. Average gray value was calculated within selected areas as the sum of the gray values of all the pixels in the selection divided by the number of pixels.

Mitochondrial Respiratory Chain Enzyme Activities by Spectrophotometer Analysis

Mitochondrial RC enzymes analysis was performed in cerebrum and cerebellum tissues as previously described (DiMauro, et al. 1987).

Nucleosides and Nucleotides Metabolic Enzymes

Thymidine phosphorylase and thymidine kinase 1 and 2 activities were measured as previously described (Marti, et al. 2003; Lopez, et al. 2009; Dorado, et al. 2011).

Statistical Methods

Data are expressed as the mean±SD of at least three experiments per group. Gehan-Breslow-Wilcoxon test was used to compare the survival proportion of each group of mice. Unpaired t-test with Welch's correction and Mann-Whitney U-test were used to compare 13-day-old $Tk2^+$ versus untreated $Tk2^{-/-}$, 13-day-old untreated $Tk2^{-/-}$ versus $Tk2^{-/-200dCMP/dTMP}$, 29-day-old wild-type versus $Tk2^{-/-200dCMP/dTMP}$ and $Tk2^{-/-400dCMP/dTMP}$, for molecular and biochemical studies. Response to treatment was evaluated comparing $Tk2^{-/-}$ versus $Tk2^{-/-200dCMP/dTMP}$ at 13 days and $Tk2^{-/-200dCMP/dTMP}$ versus $Tk2^{-/-400dCMP/dTMP}$. A P-value of <0.05 was considered to be statistically significant.

Example 2—dCMP/dTMP Delays Disease Onset, Prevents Neuromuscular Manifestations, and Prolongs Lifespan of Tk2-Deficient Mice Oral treatment with dCMP+dTMP 200 mg/kg/day each in milk ($Tk2^{-/-200dCMP/dTMP}$) beginning at postnatal day 4 delayed disease onset to 20-25 days when the mutant mice developed a mild tremor and stopped gaining weight (data not shown). In the fourth week, they manifested weakness and reduced movements. In contrast, $Tk2^{-/-}$ mice treated from day 4 with dCMP+dTMP 400 mg/kg/day each in milk ($Tk2^{-/-400dCMP/dTMP}$) appeared normal until day 21, when weight gain decelerated and mild head tremor developed (FIG. 1A).

Figure 1B:
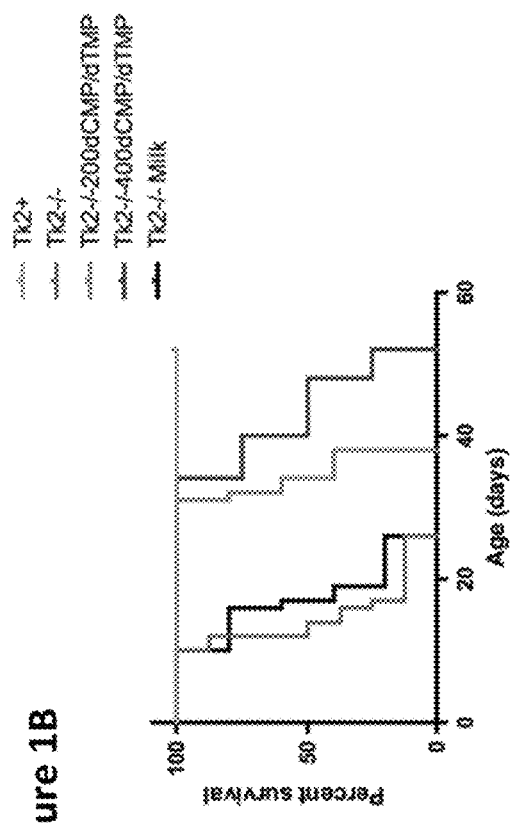
FIGS. 1C, 1D, and 1E are graphs showing the results of open-field tests for average distance traveled (FIG. 1C), ambulatory and resting times (FIG. 1D), and horizontal (XY axes) and vertical (Z-axis) movements (FIG. 1E) over 10 minutes in 29-day-old mutant and control wild-type mice treated with 200 mg/kg/day or 400 mg/kg/day of dCMP/dTMP (n=5) (Data expressed as mean±SD. Statistical analysis were performed on $Tk2^{-/-200dCMP/dTMP}$ versus $Tk2^{+200dCMP/dTMP}$ and $Tk2^{-/-400dCMP/dTMP}$ versus $Tk2^{+400dCMP/dTMP}$).

Untreated $Tk2^{-/-}$ mice had a mean lifespan of 13.2±2.5 days (mean±SD), whereas $Tk2^{-/-200dCMP/dTMP}$ survived to 34.6±3.2 days (P=0.0028; n=7; Gehan-Breslow-Wilcoxon test) while $Tk2^{-/-400dMP/dTMP}$ lived to 44.3±9.1 days (P=0.0071; n=7; Gehan-Breslow-Wilcoxon test) (FIG. 1B). The cause of death was not evident in postmortem histological studies of major organs in 29-day-old $Tk2^{-/-200dCMP/dTMP}$ mice. No adverse side effects, including malignancies, were observed in the treated homozygous, and heterozygous wild types ($Tk2^+$) and mutants except mild deceleration of weight gain in $Tk2^{+400dCMP/dTMP}$ (data not shown).

Figure 1D:
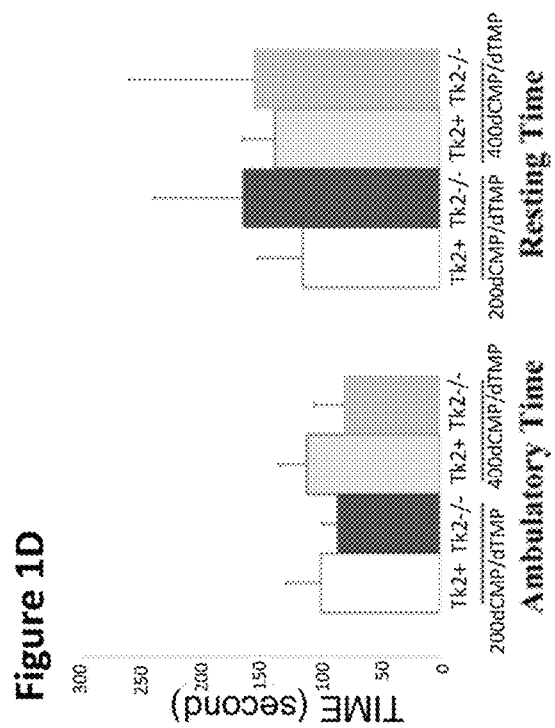
Figure 1C:
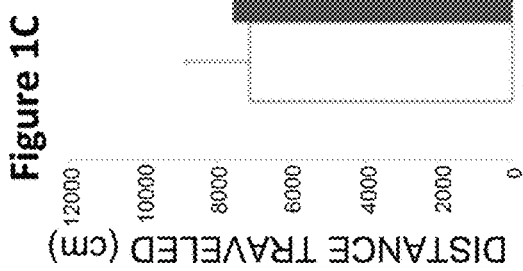

Open-field assessment of motor function in 29-day-old Tk2$^{-/-200dCMP/dTMP}$ Tk2$^{-/-400dCMP/dTMP}$, and wild-type Tk2 mice showed no differences in the distance traveled, horizontal and vertical movements, or resting time (FIGS. 1C-E).

Figure 2E:
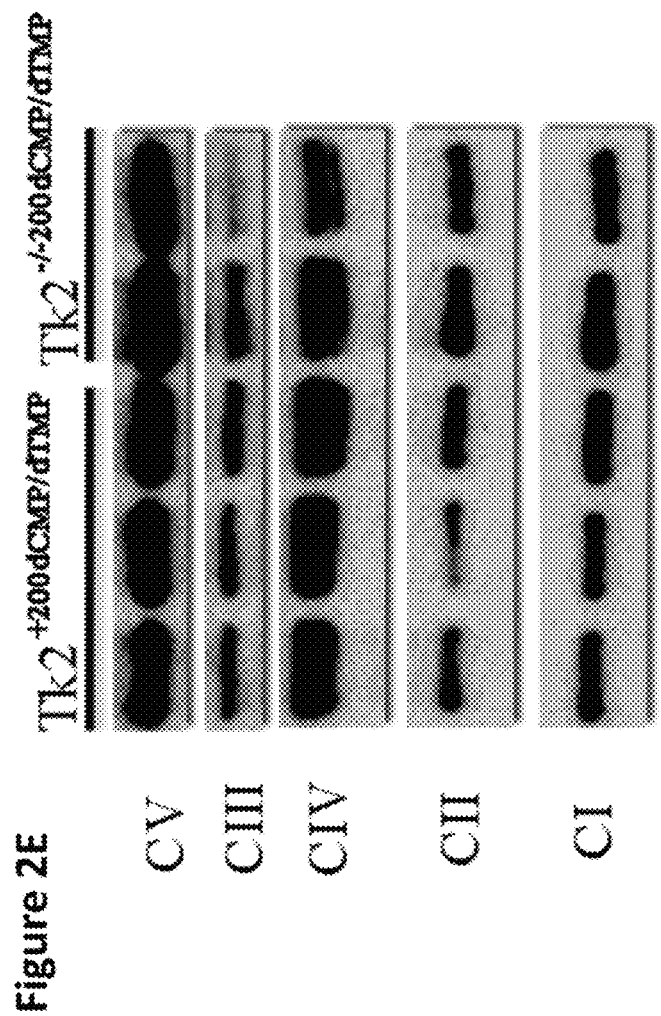
FIG. 2E shows a representative western blot of mitochondrial proteins in the muscles of $Tk2^{-/-200dCMP/dTMP}$ versus $Tk2^{+200dCMP/dTMP}$ and percentages of various proteins relative to wild-type muscle.

Relative to 29-day-old Tk2$^+$ mice, age-matched Tk2$^{-/-200dCMP/dTMP}$ and Tk2$^{-/-400dCMP/dTMP}$ animals showed decreases in gross muscle mass and muscle fiber diameter that were independent of the treatment dose but paralleled to body weight (FIG. 2). Histology showed no signs of myopathy or mitochondrial abnormalities (FIGS. 2A-D). Biochemical studies demonstrated normal mitochondrial RC activities and protein levels (FIGS. 2D-F).

Example 3—Histological and Histochemical CNS Studies Confirmed dCMP/dTMP Efficacy Efficacy of treatment in central nervous system (CNS) was demonstrated in histological studies that showed dramatic reductions in the numbers of vacuoles in neurons of the spinal cord and cerebellar and brain stem nuclei of 13-day-old Tk2$^{-/-200dCMP/dTMP}$ mice relative to untreated 13-day-old Tk2$^{-/-}$ mice (FIGS. 3A and 3B). Furthermore, cytochrome c oxidase (COX, complex IV) histochemistry of cerebellum revealed reduced overall COX activity in 13-day-old untreated Tk2$^{-/-}$ mice (FIG. 4A) with normal activities in 13- and 29-day-old Tk2$^{-/-200dCMP/dTMP}$ (FIGS. 4C and 4E) relative to Tk2$^+$ animals (FIGS. 4B, 4D, and 4F). No cell-specific immunohistochemical differences in COX protein were detected (FIGS. 4G and 4H) while severe reduction in complex I was identified by immunostaining of cerebellum of 29-day-old Tk2$^{-/-200dCMP/dTMP}$ (FIGS. 4I and 4J).

Example 4—Treatment Crosses Biological Barriers

To confirm that the treatment crosses biological barriers, dNTP levels in isolated mitochondria were assessed by polymerase extension assay described in Example 1. In 13-day-old untreated Tk2$^{-/-}$ mice relative to Tk2$^+$ littermates, isolated brain mitochondria showed decreased levels of dTTP (0.67±0.1 pmol/mg-protein versus 2.52±1.0), while isolated liver mitochondria revealed reduced dCTP levels (1.07±0.8 versus 2.9±1.0) (Table 1). The treatment crossed the blood-brain barrier increasing the level of dTTP in isolated brain mitochondria of 13-day-old Tk2$^{+200dCMP/dTMP}$ (3.55±1) and Tk2$^{-/-200dCMP/dTMP}$ (1.5±0.7) and as a consequence, restored the proportion of dTTP relative to total dNTP in treated mutants. In contrast, levels of dCTP in isolated mitochondria were stable in brain of 13-day-old Tk2$^{+200dCMP/dTMP}$ (3.07±2), decreased in brain of Tk2$^{-/-200dCMP/dTMP}$ (1.13±0.5), and decreased in liver of 13-day-old Tk2$^{+200dCMP/dTMP}$ (1.13±0.4) and Tk2$^{-/-200dCMP/dTMP}$ (0.56±0.5) (Table 1).

In 29-day-old Tk2$^{-/-200dCMP/dTMP}$ relative to Tk2$^+$ mice, absolute levels of dTTP and dCTP were markedly reduced in isolated mitochondria from brain (dTTP 0.11±0.05 and dCTP 0.6±0.2) and from liver (dTTP 0.15±0.04 and dCTP 0.04±0.03) (Table 1); when these data were expressed as percentage of total dNTPs, there were striking decreases in dTTP/dNTP in brain (P=0.0322; n=7; Mann-Whitney U-test) and dCTP/dNTP in liver (P=0.0338; n=3; Mann-Whitney U-test) (FIGS. 5A and B).

TABLE 1

| | | | | | | | |
|---|---|---|---|---|---|---|---|
| | | | | dNTP pools level in tissues | | | |
| Brain Mitochondria | Untreated Tk2$^+$ (P13; n = 5) | Untreated Tk2$^{-/-}$ (P13; n = 4) | Tk2$^{+200dCMP/dTMP}$ (P13; n = 5) | Tk2$^{-/-200dCMP/dTMP}$ (P13; n = 5) | Untreated Tk2$^+$ (P29; n = 4) | Tk2$^{+200dCMP/dTMP}$ (P29; n = 5) | Tk2$^{-/-200dCMP/dTMP}$ (P29; n = 8) |
| dATP | 0.91 ± 0.2 | 1.51 ± 1 | 0.85 ± 0.5 | 1.03 ± 0.8 | 0.44 ± 0.2 | 0.86 ± 0.4 | 0.5 ± 0.3 |
| dTTP | 2.52 ± 1 | 0.67 ± 0.1* | 3.55 ± 1 | 1.52 ± 0.7 | 1.87 ± 0.9 | 3.5 ± 1 | 0.11 ± 0.05** |
| dGTP | 1.06 ± 0.4 | 1.17 ± 0.7 | 1.9 ± 1 | 0.68 ± 0.3 | 1.3 ± 0.5 | 1.9 ± 1 | 0.87 ± 0.6 |
| dCTP | 1.99 ± 0.9 | 3.9 ± 3 | 3.07 ± 2 | 1.13 ± 0.5 | 0.32 ± 0.2 | 1.2 ± 0.6 | 0.6 ± 0.2 |
| Liver Mitochondria | Untreated Tk2$^+$ (P13; n = 3) | Untreated Tk2$^{-/-}$ (P13; n = 3) | Tk2$^{+200dCMP/dTMP}$ (P13; n = 3) | Tk2$^{-/-200dCMP/dTMP}$ (P13; n = 3) | Untreated Tk2$^+$ (P29; n = 3) | Tk2$^{+200dCMP/dTMP}$ (P29; n = 5) | Tk2$^{-/-200dCMP/dTMP}$ (P29; n = 4) |
| dATP | 1.47 ± 1 | 1.34 ± 0.8 | 1.42 ± 0.8 | 2.6 ± 1 | 0.32 ± 0.2 | 0.5 ± 0.3 | 0.31 ± 0.3 |
| dTTP | 0.61 ± 0.08 | 0.54 ± 0.2 | 0.67 ± 0.3 | 0.36 ± 0.3 | 0.46 ± 0.3 | 1.2 ± 0.8 | 0.15 ± 0.04* |
| dGTP | 2.2 ± 2 | 2.64 ± 1 | 0.93 ± 0.9 | 1.2 ± 1 | 0.58 ± 0.25 | 0.75 ± 0.4 | 0.8 ± 0.6 |
| dCTP | 2.9 ± 1 | 1.07 ± 0.8 | 1.13 ± 0.4 | 0.56 ± 0.5 | 0.36 ± 0.3 | 0.67 ± 0.2 | 0.04 ± 0.03* |

Data expressed in pmol normalized to mg-protein (mean ± SD). Statistical analyses were performed with untreated Tk2$^{-/-}$ vs untreated Tk2$^+$ (P13) and Tk2$^{-/-200dCMP/dTMP}$ vs Tk2$^{+200dCMP/dTMP}$ (P13 and P29).
* = p < 0.05;
** = p < 0.005.
P = postnatal day

Example 5—dCMP/dTMP Treatment Ameliorates Biochemical and Molecular Genetic Abnormalities Treatment with dCMP and dTMP enhanced mtDNA levels in the mutant mice. At pre-treatment baseline, 4-day-old Tk2$^{-/-}$ mice did not manifest clinical abnormalities, but showed reductions of mtDNA copy numbers in brain cerebrum (38±13% mtDNA relative to wild-type brain, P=0.0002; n=5; Mann-Whitney U-test), cerebellum (54±1%, P=0.0228; n=4; Mann-Whitney U-test), muscle (28±12%), and kidney (62±11%) with normal mtDNA levels in heart and liver (FIG. 6A). At age 13 days, untreated Tk2$^{-/-}$ animals showed marked mtDNA depletion in brain cerebrum (21±3%, P<0.0025; n=5; Mann-Whitney U-test), muscle (47±1%, P=0.0303; n=7; Mann-Whitney U-test), liver (32±1%, P=0.0140; n=5; Mann-Whitney U-test), and kidney (35±9%, P=0.008; n=6; Mann-Whitney U-test), but stable mtDNA depletion in the cerebellum (FIG. 6A). In contrast, with treatment, 13-day-old Tk2$^{-/-200dCMP/dTMP}$ mice manifested moderate mtDNA depletion only in brain cerebrum (66±34%) and normal mtDNA levels in cerebellum, muscle, heart, liver, and kidney (FIG. 6A).

At age 29 days, relative to Tk2+ mice, Tk2−/−200dCMP/dTMP mice showed mtDNA depletion that was severe in cerebellum (23±8%) and brain cerebrum (11±1%) and moderate in muscle (48±23%), liver (70±13%), and kidney (55±6%) (FIG. 6B). Compared with Tk2−/−200dCMP/dTMP mice, Tk2−/−400dCMP/dTMP animals had less severe mtDNA depletion in brain cerebrum (22±8%, P=0.0159; n=6; Mann-Whitney U-test), but similar mtDNA depletion in muscle (40±8%), liver (71±36%), and kidney (43±11%) and cerebellum (26±12%) (FIG. 6B).

To assess the impact of treatment on mitochondrial RC enzymes, their activities and steady-state protein levels in brain cerebrum and cerebellum were measured. In 13-day-old untreated Tk2−/− mice, relative to untreated wild-type, brain cerebrum showed reduced COX activity (57±19%, P=0.0159; n=5; Mann-Whitney U-test) and significantly increased citrate synthase (CS) activity (148±17%; P=0.0317; n=5; Mann-Whitney U-test) (Table 2; FIG. 7A) and, when normalized to CS, revealed decreased activities of complexes I+III (NADH-cytochrome c reductase) (76±0.06%, P=0.0159; n=5; Mann-Whitney U-test) and II+III (succinate-cytochrome c reductase) (72±9%) in addition to IV (41±14%, P=0.0079; n=5; Mann-Whitney U-test) (Table 2; FIG. 7B).

The RC defects were more severe in cerebellum with significant reductions in all of the complexes when normalized either to CS (FIG. 7C) or to mg-proteins with predominant defect in complex I (29±15%; P=0.0087; n=5; Unpaired t-test with Welch's correction) and increased CS activity (129±34%) (Table 3). In contrast, 13-day-old Tk2−/−200dCMP/dTMP had normal RC enzyme activities in brain cerebrum (Table 2; FIGS. 7A and 7B) and only a mild defect in complex I (56±21%) in cerebellum compared with age-matched treated control mice (Table 3; FIG. 7C). In 29-day-old Tk2−/−200dCMP/dTMP, activities of RC enzymes were normal in brain cerebrum (Table 2). In contrast, cerebellum of Tk2−/−200dCMP/dTMP manifested a mild defect in complex IV (62±20%) and severe defect in complex I+III (35±24%, P=0.0296; n=5; Mann-Whitney U-test), while RC activities were completely rescued in the Tk2−/−400dCMP/dTMP (Table 3; FIG. 7C).

Figure 7H:
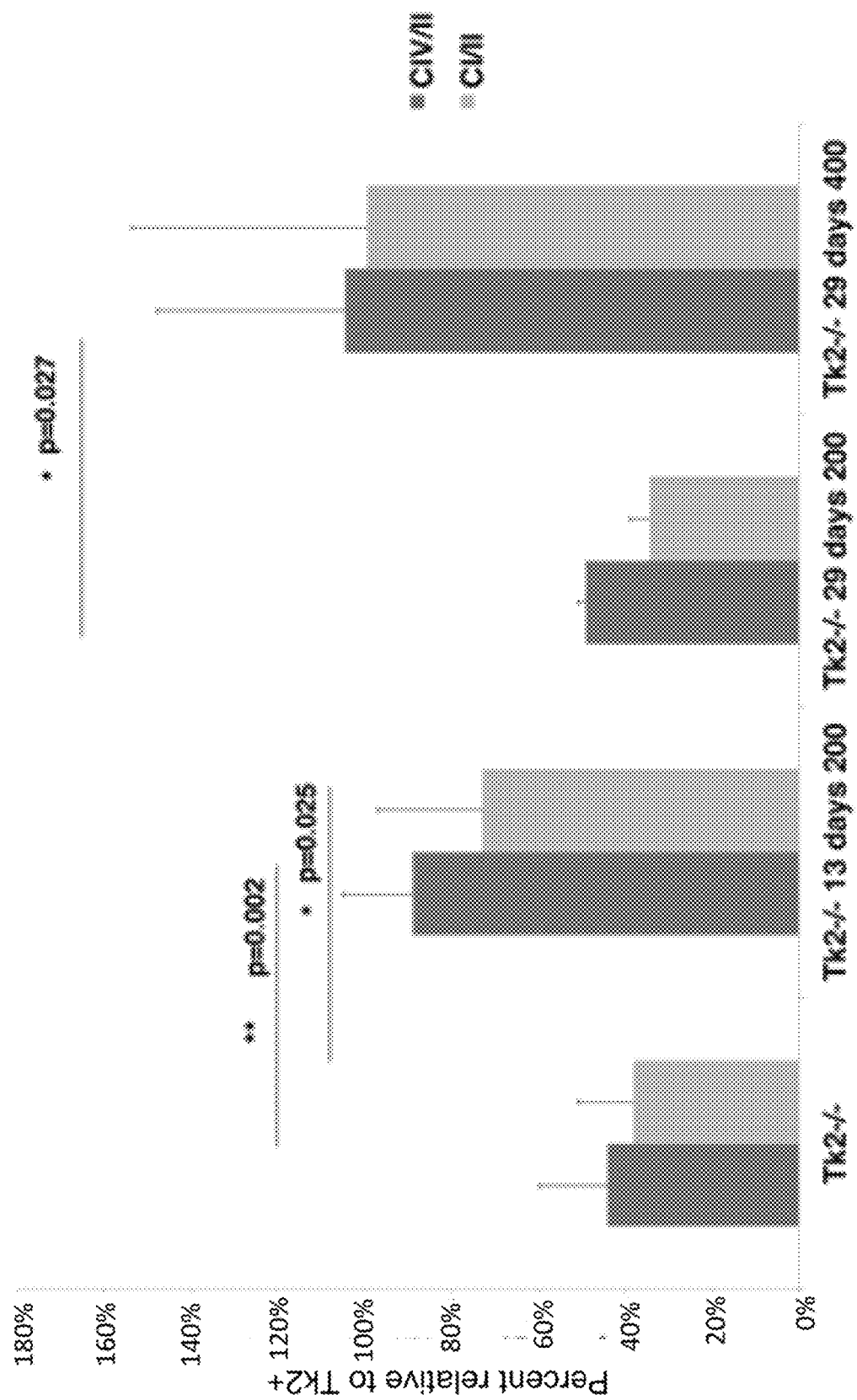

Western blot analysis of mitochondrial RC complex subunits in 13-day-old untreated Tk2−/− animals compared with untreated control mice revealed reductions in steady-state levels of complex I (55±39% brain cerebrum; 38±13% cerebellum, P=0.025; n=6; Mann-Whitney U-test) and complex IV (74±32% brain cerebrum; 44±16% cerebellum, P=0.0017; n=6; Mann-Whitney U-test), while RC protein levels were normal in 13-day-old Tk2−/−200dCMP/dTMP mice (FIGS. 7D-7F and 7H). In 29-day-old Tk2−/−200dCMP/dTMP compared with Tk2+200dCMP/dTMP a reduced levels of subunits of complexes I (45%±2, P=0.0196; n=4; Mann-Whitney U-test) and III (69%±2) were observed in brain cerebrum (FIG. 7G) and complexes I (34%±4) and IV (49%±1, P=0.0267; n=4; Unpaired t-test with Welch correction) in cerebellum (FIG. 7H). In 29-day-old Tk2−/−400dCMP/dTMP, a complete rescue of the RC defect was observed when compared to Tk2+400dCMP/dTMP.

TABLE 2

Mitochondrial respiratory chain enzyme activities in brain hemisphere

| Normalized to mg-proteins | Untreated Tk2+ (P13; n = 5) | Untreated Tk2−/− (P13; n = 5) | Tk2+200dCMP/dTMP (P13; n = 4) | Tk2−/−200dCMP/dTMP (P13; n = 5) | Tk2+200dCMP/dTMP (P29; n = 4) | Tk2−/−200dCMP/dTMP (P29; n = 6) |
|---|---|---|---|---|---|---|
| Complex I | 0.05 ± 0.01 | 0.05 ± 0.03 | 0.04 ± 0.0.03 | 0.07 ± 0.03 | 0.24 ± 0.13 | 0.29 ± 0.06 |
| Complex I + III | 0.79 ± 0.1 | 0.88 ± 0.1 | 0.60 ± 0.1 | 0.89 ± 0.4 | 0.62 ± 0.38 | 0.71 ± 0.16 |
| Complex II + III | 0.36 ± 0.04 | 0.38 ± 0.03 | 0.33 ± 0.03 | 0.30 ± 0.06 | 0.47 ± 0.05 | 0.44 ± 0.01 |
| Complex IV | 0.3 ± 0.1* | 0.17 ± 0.05* | 0.17 ± 0.1 | 0.22 ± 0.13 | 1.98 ± 0.29 | 1.55 ± 0.17 |
| Complex II | 0.4 ± 0.1 | 0.51 ± 0.1 | 0.27 ± 0.1 | 0.43 ± 0.06 | 0.98 ± 0.18 | 0.79 ± 0.04 |
| CS | 5.3 ± 1** | 7.5 ± 1** | 6.05 ± 0.8 | 7.2 ± 1 | 7.2 ± 1.2 | 7.09 ± 0.9 |
| Normalized to CS | Untreated Tk2+ (P13; n = 5) | Untreated Tk2−/− (P13; n = 5) | Tk2+200dCMP/dTMP (P13; n = 4) | Tk2−/−200dCMP/dTMP (P13; n = 5) | Tk2+200dCMP/dTMP (P29; n = 4) | Tk2−/−200dCMP/dTMP (P29; n = 6) |
| Complex I | 0.009 ± 0.003 | 0.007 ± 0.003 | 0.007 ± 0.004 | 0.01 ± 0.005 | 0.03 ± 0.022 | 0.042 ± 0.009 |
| Complex I + III | 0.15 ± 0.05 | 0.11 ± 0.01 | 0.1 ± 0.03 | 0.12 ± 0.056 | 0.08 ± 0.04 | 0.1 ± 0.02 |
| Complex II + III | 0.07 ± 0.014 | 0.05 ± 0.006* | 0.05 ± 0.01 | 0.04 ± 0.01 | 0.066 ± 0.011 | 0.062 ± 0.007 |
| Complex IV | 0.057 ± 0.03 | 0.02 ± 0.008* | 0.028 ± 0.01 | 0.03 ± 0.017 | 0.28 ± 0.06 | 0.22 ± 0.04 |
| Complex II | 0.07 ± 0.02 | 0.069 ± 0.01 | 0.045 ± 0.019 | 0.06 ± 0.017 | 0.14 ± 0.03 | 0.11 ± 0.01 |
| Normalized to II | Untreated Tk2+ (P13; n = 5) | Untreated Tk2−/− (P13; n = 5) | Tk2+200dCMP/dTMP (P13; n = 4) | Tk2−/−200dCMP/dTMP (P13; n = 5) | Tk2+200dCMP/dTMP (P29; n = 4) | Tk2−/−200dCMP/dTMP (P29; n = 6) |
| Complex I | 0.13 ± 0.05 | 0.11 ± 0.07 | 0.11 ± 0.04 | 0.18 ± 0.1 | 0.25 ± 0.12 | 0.37 ± 0.08 |
| Complex I + III | 2.07 ± 0.6 | 1.75 ± 0.3 | 2.34 ± 0.5 | 2.06 ± 0.9 | 0.74 ± 0.7 | 0.89 ± 0.15 |
| Complex II + III | 0.97 ± 0.25 | 0.76 ± 0.15 | 1.37 ± 0.4 | 0.7 ± 0.05 | 0.50 ± 0.15 | 0.55 ± 0.02 |

TABLE 2-continued

Mitochondrial respiratory chain enzyme activities in brain hemisphere

| Complex IV | 0.79 ± 0.3  | 0.36 ± 0.1  | 0.66 ± 0.3 | 0.55 ± 0.3  | 2.06 ± 0.4 | 1.96 ± 0.13 |
|------------|-------------|-------------|------------|-------------|------------|-------------|
| CS         | 14.2 ± 4.2  | 15.01 ± 3.2 | 19.4 ± 4.6 | 17.05 ± 4.1 | 7.78 ± 3   | 8.9 ± 1.2   |

Data expressed in micromole/min/mg tissue and normalized to mg-proteins (mean ± SD) or normalized to citrate synthase (CS) activity or to complex II activity (mean ± SD). Statistical analyses were performed with untreated $Tk2^{-/-}$ vs untreated $Tk2^+$ (P13) and $Tk2^{-/-200dCMP/dTMP}$ vs $Tk2^{+200dCMP/dTMP}$ (P13 and P29).
* = p < 0.05;
** = p < 0.005).
P = postnatal day

TABLE 3

Cerebellar mitochondrial respiratory chain enzyme activities

| Normalized to CS | COX | I | II + III | II | I + III |
|---|---|---|---|---|---|
| $Tk2^+$ | 0.24 ± 0.07 | 0.08 ± 0.03 | 0.11 ± 0.02 | 0.11 ± 0.03 | 0.14 ± 0.03 |
| $Tk2^{-/-}$ | 0.13 ± 0.07* | 0.015 ± 0.01** | 0.06 ± 0.02* | 0.06 ± 0.01* | 0.067 ± 0.05* |
| $Tk2^{+13\ days}\ 200$ | 0.24 ± 0.07 | 0.065 ± 0.04 | 0.11 ± 0.03 | 0.11 ± 0.003 | 0.11 ± 0.06 |
| $Tk2^{-/-13\ days}\ 200$ | 0.19 ± 0.01 | 0.036 ± 0.01 | 0.10 ± 0.02 | 0.087 ± 0.06 | 0.11 ± 0.01 |
| $Tk2^{+29\ days}$ | 0.20 ± 0.02 | 0.069 ± 0.007 | 0.072 ± 0.004 | 0.073 ± 0.008 | 0.10 ± 0.01 |
| $Tk2^{+29\ days}\ 200$ | 0.17 ± 0.03 | 0.049 ± 0.004 | 0.071 ± 0.02 | 0.065 ± 0.01 | 0.11 ± 0.03 |
| $Tk2^{-/-29\ days}\ 200$ | 0.11 ± 0.03* | 0.034 ± 0.01 | 0.057 ± 0.01 | 0.080 ± 0.02 | 0.05 ± 0.005* |
| $Tk2^{+29\ days}$ | 0.027 ± 0.002 | 0.002 ± 0.002 | 0.039 ± 0.009 | 0.07 ± 0.01 | 0.028 ± 0.002 |
| $Tk2^{+29\ days}\ 400$ | 0.036 ± 0.022 | 0.005 ± 0.001 | 0.017 ± 0.012 | 0.035 ± 0.02 | 0.027 ± 0.019 |
| $Tk2^{-/-29\ days}\ 400$ | 0.04 ± 0.024 | 0.004 ± 0.002 | 0.02 ± 0.006 | 0.05 ± 0.01 | 0.028 ± 0.019 |

| Normalized to II | COX | I | II + III | CS | I + III |
|---|---|---|---|---|---|
| $Tk2^+$ | 2.1 ± 0.6 | 0.74 ± 0.3 | 1.01 ± 0.1 | 9.1 ± 2.5 | 1.31 ± 0.2 |
| $Tk2^{-/-}$ | 2.1 ± 0.7 | 0.29 ± 0.2 | 1.06 ± 0.1 | 18.5 ± 7.4 | 0.97 ± 0.6 |
| $Tk2^{+13\ days}\ 200$ | 2.09 ± 0.2 | 0.43 ± 0.3 | 0.98 ± 0.1 | 9.1 ± 2.5 | 0.92 ± 0.3 |
| $Tk2^{-/-13\ days}\ 200$ | 1.7 ± 0.4 | 0.29 ± 0.1 | 0.84 ± 0.0.5 | 8.8 ± 1.8 | 0.94 ± 0.1 |
| $Tk2^{+29\ days}$ | 2.8 ± 0.02 | 0.95 ± 0.003 | 0.99 ± 0.1 | 13.7 ± 1.5 | 1.48 ± 0.08 |
| $Tk2^{+29\ days}\ 200$ | 2.62 ± 0.38 | 0.65 ± 0.4 | 0.97 ± 0.1 | 15.9 ± 3.6 | 1.76 ± 0.2 |
| $Tk2^{-/-29\ days}\ 200$ | 1.43 ± 0.4 | 0.43 ± 0.2 | 0.72 ± 0.1 | 13.3 ± 3.5 | 0.68 ± 0.2 |
| $Tk2^{+29\ days}$ | 0.38 ± 0.05 | 0.031 ± 0.04 | 0.53 ± 0.04 | 14 ± 2.2 | 0.4 ± 0.03 |
| $Tk2^{+29\ days}\ 400$ | 0.43 ± 0.3 | 0.14 ± 0.02 | 0.35 ± 0.03 | 16 ± 4.3 | 0.56 ± 0.3 |
| $Tk2^{-/-29\ days}\ 400$ | 0.47 ± 0.3 | 0.05 ± 0.06 | 0.41 ± 0.01 | 19.4 ± 3.4f | 0.5 ± 0.2 |

Data expressed in micromole/min/mg tissue and normalized to mg-proteins or normalized to citrate synthase (CS) activity or to complex II activity (mean ± SD). Statistical analyses were performed with untreated $Tk2^{-/-}$ vs untreated $Tk2^+$ and $Tk2^{-/-200dCMP/dTMP}$ vs $Tk2^{+200dCMP/dTMP}$.
*= p < 0.05;
**= p < 0.005)
P = postnatal day Example 6—Deoxynucleotide Metabolism To understand the metabolism of dCMP/dTMP after oral gavage administration, levels of dCMP/dTMP and their metabolites in muscle and liver tissues and in plasma were measured after 30 minutes of oral gavage. In $Tk2^{-/-200dCMP/dTMP}$ mice, deoxynucleoside monophosphates were not detectable. Levels of deoxyuridine and deoxythymidine were markedly increased at age 13 days, but subsequently lower in 29-day-old mice (FIGS. 8A-8C). Thymidine phosphorylase (TP) degrades deoxyuridine and deoxythymidine, respectively, to uracil and thymine plus deoxyribose 1-phosphate (Brown and Bicknell 1998; Hirano, et al. 2004).

To understand the cause for differences in deoxyuridine and deoxythymidine plasma levels between 13 and 29 days of age, the activity level of TP in small intestine, brain, and liver was measured. TP activity was higher in the small intestine at P29 (FIG. 8D), but unchanged in brain and liver tissues (Table 4). Therefore, intestinal TP is responsible for the rapid catabolism of deoxyuridine and deoxythymidine at P29 and the resulting reduced plasma levels.

Tk2 activity was confirmed to be normal in treated and untreated $Tk2^+$ mice and reduced in $Tk2^{-/-}$ mice in muscle and brain. Unexpectedly, Tk1 activity was increased in brain and muscle of 13- and 29-day-old treated mice (FIGS. 8E and 8F).

TABLE 4

Deoxypyrimidine monophosphates metabolism

Plasma Levels of nucleoside metabolites

| Mice | Age | Treatment | Dose | Time | Uracil (μM) | Thymine (μM) | dUrd (μM) | Thd (μM) |
|---|---|---|---|---|---|---|---|---|
| $Tk2^+$ (N = 1) | 13 | dCMP + dTMP | 80 nmol/kg/day | 0 | 19.1 | UND | 5.5 | 1.0 |
| $Tk2^+$ (N = 3) | 13 | dCMP + dTMP | 80 nmol/kg/day | 30 | 59.3 ± 33.9 | 3.6 ± 3.3 | 29.0 ± 18.5 | 71.6 ± 53.3 |
| $Tk2^{-/-}$ (N = 1) | 13 | dCMP + dTMP | 80 nmol/kg/day | 0 | 21.2 | 5.0 | 4.2 | 6.8 |
| $Tk2^{-/-}$ (N = 3) | 13 | dCMP + dTMP | 80 nmol/kg/day | 30 | 78.0 ± 56.7 | 5.4 ± 3.5 | 28.3 ± 9.1 | 70.4 ± 19.2 |
| $Tk2^+$ (N = 3) | 29 | dCMP + dTMP | 80 nmol/kg/day | 0 | 79.7 ± 20.5 | 0.1 ± 0.1 | 2.2 ± 0.1 | 5.0 ± 5.4 |

TABLE 4-continued

| Deoxypyrimidine monophosphates metabolism | | | | | | | | |
|---|---|---|---|---|---|---|---|---|
| Tk2$^+$ (N = 2) | 29 | dCMP + dTMP | 80 nmol/kg/day | 30 | 109.3 ± 1.3 | 68.7 ± 53.3 | 29.3 ± 13.4 | 73.4 ± 50.2 |
| Tk2$^{-/-}$ (N = 3) | 29 | dCMP + dTMP | 80 nmol/kg/day | 30 | 61.4 ± 10.9 | 11.2 ± 3.4 | 18 ± 1.9 | 30.8 ± 13.2 |

| Thymidine Phosphorylase activity | | | | | |
|---|---|---|---|---|---|
| Mice | Age | Treatment | Dose | TISSUE | Activity (nmol/h/mg-proteins) |
| Tk2$^+$ (N = 3) | 13 | dCMP + dTMP | 80 nmol/kg/day | BRAIN | 6.2 ± 3.3 |
| Tk2$^{-/-}$ (N = 4) | 13 | dCMP + dTMP | 80 nmol/kg/day | BRAIN | 11.6 ± 0.8 |
| Tk2$^+$ (N = 2) | 29 | dCMP + dTMP | 80 nmol/kg/day | BRAIN | 5.9 ± 0.4 |
| Tk2$^{-/-}$ (N = 2) | 29 | dCMP + dTMP | 80 nmol/kg/day | BRAIN | 8.0 ± 0.8 |
| Tk2$^+$ (N = 4) | 13 | Untreated | — | LIVER | 4.9 ± 2.4 |
| Tk2$^{-/-}$ (N = 2) | 13 | Untreated | — | LIVER | 6.1 ± 2.6 |
| Tk2$^+$ (N = 3) | 13 | dCMP + dTMP | 80 nmol/kg/day | LIVER | 9.0 ± 2.9 |
| Tk2$^{-/-}$ (N = 3) | 13 | dCMP + dTMP | 80 nmol/kg/day | LIVER | 6.0 ± 3.1 |
| Tk2$^+$ (N = 6) | 29 | dCMP + dTMP | 80 nmol/kg/day | LIVER | 4.9 ± 2.45 |
| Tk2$^{-/-}$ (N = 4) | 29 | dCMP + dTMP | 80 nmol/kg/day | LIVER | 4.6 ± 2.5 |
| Tk2$^+$ (N = 6) | 13 | Untreated | — | S.I. | 26.1 ± 11.0 |
| Tk2$^{-/-}$ (N = 3) | 13 | Untreated | — | S.I. | 28 ± 14 |
| Tk2$^+$ (N = 2) | 13 | dCMP + dTMP | 80 nmol/kg/day | S.I. | 29.6 ± 3.9 |
| Tk2$^{-/-}$ (N = 3) | 13 | dCMP + dTMP | 80 nmol/kg/day | S.I. | 30.9 ± 10.6 |
| Tk2$^+$ (N = 9) | 29 | dCMP + dTMP | 80 nmol/kg/day | S.I. | 278.8 ± 75 |
| Tk2$^{-/-}$ (N = 4) | 29 | dCMP + dTMP | 80 nmol/kg/day | S.I. | 244.1 ± 80 |

S.I. = small intestine;
dUrd = deoxyuridine;
Thd = thymidine

Example 7—Materials and Protocols Used for Examples 8-10

The compounds used in Examples 8-10 were dTMP.Na$_2$ and dCMP.Na$_2$ were obtained through Hongene Biotechnology USA, Inc. (Morrisville, N.C.). The compounds were verified as greater than 99% pure by HILPC and by mass spectrometry. Each bottle of dTMP.Na$_2$, and dCMP.Na$_2$ was labeled with the following but not limited to: the product name, product lot number, protocol number, recommended storage conditions, expiration date, "Caution: New Drug-Limited by Federal Law to Investigational Use," Hongene Biotech' company name and address, and the Investigator's name or investigation site. Labeling complied with the requirements of 21 CFR 312.6.

The Investigator ensured that all study drugs were stored and dispensed in accordance with the Food and Drug Administration (FDA) regulations concerning the storage and administration of investigational drugs.

Example 8—dTMP and dCMP Treatment on Patients—Case 1

The first patient was a 29 year-old Spanish man (JJM) with TK2 deficiency that initially manifested at age 3 years with leg weakness causing difficulty running and frequent falls (Vilá, et al. 2003). The weakness progressed at age 12, began using BiPAP ventilatory support and one year later, he became wheelchair-bound. Because of arm weakness, he stopped playing the violin and due to respiratory muscle weakness, he has suffered recurrent bouts of pneumonia and uses BiPAP 23 hours daily. Despite the severe myopathy, this young man completed medical school.

In August, 2011, he began dTMP and dCMP (each 100 mg/kg/day supplied by Hongene Biotechnology as described in Example 7), and the dose was increased to 200 mg/kg/day. The compounds were mixed in water and administered orally as a single daily dose. After initiating this therapy, the patient increased weight from a baseline of 35 kg to 44 kg, muscle strength improved slightly at the biceps, triceps, and quadriceps and he reduced time on BiPAP from 24 to 22 hours daily. During this period, he developed hearing loss, which was likely due to disease progression as this clinical manifestation has been reported in another patient with TK2 deficiency (Marti et al., 2010). No other potential side-effects were noted by this patient.

Example 9—dTMP and dCMP Treatment on Patients—Case 2

The second patient was a 10 year-old Italian boy (LS DOB Jun. 3, 2004) who presented at age 2 years with hypotonia, severe limb weakness, and delayed motor development. He was relatively stable and was able to sit and walk unassisted until September, 2011, when he became very weak and lost the ability to walk. He was barely able to stand without support. In March, 2012, he started dTMP+ dCMP therapy (dTMP and dCMP (each 100 mg/kg/day supplied by Hongene Biotechnology as described in Example 7). The compounds were mixed in water and administered orally as a single daily dose, which was prescribed by an Italian physician. In August, 2012, significant improvement of strength was noted. He was able to walk 10 steps independently. In addition to the improved limb strength, his voice and head control improved. He grew 5 centimeters in height and gained 3.5 kilograms in weight. In November, 2012, the doses were increased to 200 mg/kg/day. In late 2014, his 6-minute walk test showed a 3-fold improvement over pre-treatment baseline. As of March, 2016, he is able to walk unassisted, climb stairs using arm rails for support, ride a bicycle, and swim.

Example 10—dTMP and dCMP Treatment on Patients—Case 3

A third patient was a 3 year-old child (AE, DOB Feb. 11, 2011) with infantile-onset myopathy. He had documented mtDNA depletion (11% of normal in skeletal muscle), and compound heterozygous mutations in the TK2 gene: c.144_145DelGA mutation which causes a frameshift, and c.323C>T missense mutation (p.T108M) (identified in the Medical Genetics Laboratory at the Baylor College of Medicine). The child developed normally until age 11 months, when he was able to pull to a standing position and walk a few steps using his arms to hold onto furniture. He lost the ability to walk and has become unable to sit, stand, roll over in bed, or lift his limbs or head off of a bed. Baseline serum creatine kinase levels were 1290-2098 U/L and venous lactate was elevated at 3.9 mmol/L (normal 0.5-2.2). The diagnosis of mitochondrial disease was made at Johns Hopkins Medical Center in May, 2012, when a muscle biopsy revealed severe cytochrome c oxidase (complex IV) deficiency. He started a cocktail of coenzyme Q10, L-carnitine, and creatine, which did not lead to significant improvements. The diagnosis of TK2 deficiency was achieved by genetic test results in July, 2012. After developing an upper respiratory viral infection on September 2012, he was put on non-invasive ventilation and subsequently received a tracheostomy and placed on mechanical ventilation.

An emergency IND was requested on Oct. 24, 2012 to initiate dCMP+dTMP therapy in AE. At that time, he weighed 10.4 kg and was unable to grip objects or lift his legs from the bed. An eIND was obtained and he started the therapy in November, 2012 at 100 mg/kg/day. One month later, the doses were increased to 200 mg/kg/day. He showed improvement in his, weight, arm strength and leg movements. At age 4 years 9 months, he weighed 19.5 kg and was able to grip and hold small objects, lift his arm using triceps muscle, and lift his legs from the bed.

REFERENCES

Akman, et al. (2008) Thymidine kinase 2 (H11126N) knock in mice show the essential role of balanced deoxynucleotide pools for mitochondrial DNA maintenance. *Hum Mol Genet* 17:2433-2440

Alston, et al. (2013) Late-onset respiratory failure due to TK2 mutations causing multiple mtDNA deletions. *Neurology.* 81:2051-3

Bartesaghi, et al. (2010) Loss of thymidine kinase 2 alters neuronal bioenergetics and leads to neurodegeneration. *Hum Mol Genet.* 19:1669-77

Béhin, et al. (2012) Adult cases of mitochondrial DNA depletion due to TK2 defect An expanding spectrum. *Neurology* 78:644-648

Blakely, et al. (2008) Novel mutations in the TK2 gene associated with fatal mitochondrial DNA depletion myopathy. *Neuromuscular Disorders* 18:557-560

Bourdon, et al. (2007) Mutation of RRM2B, encoding p53-controlled ribonucleotide reductase (p53R2), causes severe mitochondrial DNA depletion. *Nat Genet* 39: 776-780

Brown, Bicknell. (1998) Thymidine phosphorylase, 2-deoxy-D-ribose and angiogenesis. *Biochem J* 334: 1-8

Carrozzo, et al. (2003) Mutation analysis in 16 patients with mtDNA depletion. *Hum Mutat* 21:453-454

Chanprasert, et al. (2013) Molecular and clinical characterization of the myopathic form of mitochondrial DNA depletion syndrome caused by mutations in the thymidine kinase (TK2) gene. *Mol Genet Metab.* 110:153-61

Chanprasert, et al. (2012) TK2-Related Mitochondrial DNA Depletion Syndrome, Myopathic Form. *GeneReviews® Internet*, Dec. 6, 2012

Collins, et al. (2009) Progressive myofiber loss with extensive fibro-fatty replacement in a child with mitochondrial DNA depletion syndrome and novel thymidine kinase 2 gene mutations. *Neuromuscular Disorders* 19:784-787

Copeland (2008) Inherited mitochondrial diseases of DNA replication. *Ann. Rev. Med.* 59:131-146

DiMauro, et al. (1987) Cytochrome c oxidase deficiency in Leigh syndrome. *Ann Neurol* 22: 498-506

Di Mauro, Schon. (2003) Mitochondrial respiratory-chain diseases. *N Engl J Med* 348:2656-2668

DiMauro, Hirano. (2005) Mitochondrial encephalomyopathies: an update. *Neuromnscul Disord* 15:276-286

Dorado, et al. (2011) Onset and organ specificity of Tk2 deficiency depends on Tk1 down-regulation and transcriptional compensation. *Hum Mol Genet.* 20:155-64

Elpeleg, et al. (2005) Deficiency of the ADP-forming succinyl-CoA synthase activity is associated with encephalomyopathy and mitochondrial DNA depletion. *Am J Hum Genet* 76: 1081-1086

Ferraro, et al. (2010) Quantitation of cellular deoxynucleoside triphosphates. *Nucleic Acids Research* 38: e85

Galbiali, et al. (2006) New mutations in TK2 gene associated with mitochondrial DNA depletion. *Pediatr Neurol* 34: 177-185

Garone, et al (2014) Deoxypyrimidine monophosphate bypass therapy for thymidine kinase 2 deficiency. *EMBO Mol Med* 6:1016-1027

Gotz, et al. (2008) Thymidine kinase 2 defects can cause multi-tissue mtDNA depletion syndrome. *Brain* 131: 2841-2850

Hirano, et al. (2001) Defects of intergenomic communication: autosomal disorders that cause multiple deletions and depletion of mitochondrial DNA. *Semin Cell Develop Biol* 12:417-427

Hirano, et al. (2004) MtDNA maintenance and stability genes: MNGIE and mtDNA depletion syndromes. In: Köhler, Bauer, editors. Mitochondrial Function and Biogenetics. Berlin: Springer-Verlag. p. 177-200

Leshinsky-Silver, et al. (2008) A defect in the thymidine kinase 2 gene causing isolated mitochondrial myopathy without mtDNA depletion. *Eur J Paediatr Neurol* 12:309-13

Lesko, et al. (2010) Two novel mutations in thymidine kinase-2 cause early onset fatal encephalomyopathy and severe mtDNA depletion. *Neuromuscul Disord* 20:198-203

Lopez, et al. (2009) Unbalanced deoxynucleotide pools cause mitochondrial DNA instability in thymidine phosphorylase deficient mice. *Hum Mol Genet* 18: 714-722

Mancuso, et al. (2002) Mitochondrial DNA depletion: mutations in thymidine kinase gene with myopathy and SMA. *Neurology.* 59:1197-202

Mancuso, et al. (2003) Mitochondrial myopathy of childhood associated with mitochondrial DNA depletion and a homozygous mutation (T77M) in the TK2 gene. *Arch Neurol.* 60:1007-9

Mandel, et al. (2001) The deoxyguanosine kinase gene is mutated in individuals with depleted hepatocerebral mitochondrial DNA. *Nat Genet* 29: 337-341

Marti, et al. (2010) Hearing loss in a patient with the myopathic form of mitochondrial DNA depletion syndrome and a novel mutation in the TK2 gene. *Pediatr Res.* 68:151-4

Marti, et al. (2012) Measurement of mitochondrial dNTP pools. *Methods Mol Biol* 837: 135-148

Marti, et al. (2003) Alterations of nucleotide metabolism: A new mechanism for mitochondrial disorders. *Clin Chem Lab Med.* 41:845-51

Naviaux, Nguyen. (2004) POLG mutations associated with Alpers' syndrome and mitochondrial DNA depletion. *Ann Neurol* 55: 706-712

Oskoui, et al. (2006) Clinical spectrum of mitochondrial DNA depletion due to mutations in the thymidine kinase 2 gene. *Arch Neurol* 63:1122-1126.

Ostergaard, et al. (2007) Deficiency of the alpha subunit of succinate-coenzyme A ligase causes fatal infantile lactic acidosis with mitochondrial DNA depletion. *Am J Hum Genet* 81: 383-387

Paradas, et ac. (2012) TK2 mutation presenting as indolent myopathy. *Neurology* 29:504-506

Roos, et al. (2014) Mitochondrial DNA depletion in single fibers in a patient with novel TK2 mutations. *Neuromuscul Disord.* 24:713-20

Saada, et al. (2001) Mutant mitochondrial thymidine kinase in mitochondrial DNA depletion myopathy. *Nat Genet* 29:342-344

Saada, et al. (2003) Mitochondrial deoxyribonucleoside triphosphate pools in thymidine kinase 2 deficiency. *Biochem Biophys Res Commun* 310:963-966

Sarzi, et al. (2007) Twinkle helicase (PEO1) gene mutation causes mitochondrial DNA depletion. *Ann Neurol.* 62: 579-587

Spinazzola, et al. (2006) MPV17 encodes an inner mitochondrial membrane protein and is mutated in infantile hepatic mitochondrial DNA depletion. *Nat Genet* 38: 570-575

Tulinius, et al. (2005) Novel mutations in the thymidine kinase 2 gene (TK2) associated with fatal mitochondrial myopathy and mitochondrial DNA depletion. *Neuromnuscul Disord.* 15:412-415

Tyynismaa, et al. (2012) Thymidine kinase 2 mutations in autosomal recessive progressive external ophthalmoplegia with multiple mitochondrial DNA deletions. *Hum Mol Genet* 21:66-75

Vilá, et al. (2003) Reversion of mtDNA depletion in a patient with TK2 deficiency. *Neurology* 60:1203-1205

Wang, et al. (2005) Molecular insight into mitochondrial DNA depletion syndrome in two patients with novel mutations in the deoxyguanosine kinase and thymidine kinase 2 genes. *Mol Genet Metab.* 84:75-82.

The invention claimed is:

1. A method of treating thymidine kinase 2 (TK2) deficiency in a subject in need thereof comprising administering to the subject a therapeutically effective amount of a composition comprising thymidine-5'-monophosphate (TMP) and 2'-deoxycytidine-5'-monophosphate (dCMP).

2. The method of claim 1, wherein the subject is a mammal.

3. The method of claim 1, wherein the subject is a human.

4. The method of claim 1, wherein the therapeutically effective amount is between about 100 mg/kg/day and about 1000 mg/kg/day.

5. The method of claim 4, wherein the composition comprises mixtures of TMP and dCMP and the therapeutically effective amount is between about 100 mg/kg/day and about 1000 mg/kg/day of each deoxyribonucleoside monophosphate in the composition.

6. The method of claim 4, wherein the composition comprises mixtures of TMP and dCMP and the therapeutically effective amount is between about 100 mg/kg/day and about 1000 mg/kg/day of the total deoxyribonucleoside monophosphates in the composition.

7. The method of claim 1, wherein the therapeutically effective amount is between about 200 mg/kg/day and about 800 mg/kg/day.

8. The method of claim 7, wherein the composition comprises mixtures of TMP and dCMP and the therapeutically effective amount is between about 200 mg/kg/day and about 800 mg/kg/day of each deoxyribonucleoside monophosphate in the composition.

9. The method of claim 7, wherein the composition comprises mixtures of TMP and dCMP and the therapeutically effective amount is between about 200 mg/kg/day and about 800 mg/kg/day of the total deoxyribonucleoside monophosphates in the composition.

10. The method of claim 1, wherein the therapeutically effective amount is between about 250 mg/kg/day and about 400 mg/kg/day.

11. The method of claim 10, wherein the composition comprises mixtures of TMP and dCMP and the therapeutically effective amount is between about 250 mg/kg/day and about 400 mg/kg/day of each deoxyribonucleoside monophosphate in the composition.

12. The method of claim 10, wherein the composition comprises mixtures of TMP and dCMP and the therapeutically effective amount is between about 250 mg/kg/day and about 400 mg/kg/day of the total deoxyribonucleoside monophosphates in the composition.

13. The method of claim 1, wherein the composition is administered once daily, twice daily, three times daily, four times daily, five times daily or six times daily.

14. The method of claim 1, wherein the composition administered orally, intrathecally, enterally, or intravenously.

15. The method of claim 14, further comprising wherein the composition is administered orally and comprises deoxyribonucleoside monophosphates mixed with cow's milk, human breast milk, infant formula or water.

16. The method of claim 1, further comprising administering to the subject an inhibitor of thymidine phosphorylase.

17. The method of claim 16, wherein the inhibitor of thymidine phosphorylase is tipiracil.

18. The method of claim 1, further comprising administering to the subject an inhibitor of cytidine deaminase.

19. The method of claim 18, wherein the inhibitor of cytidine deaminase is tetrahydrouridine [THU].

20. The method of claim 1, wherein the therapeutically effective amount of the composition administered to the subject is increased over time.

21. The method of claim 20, wherein a first therapeutically effective amount of the composition administered to the subject is about 100 mg/kg/day of composition, and wherein the therapeutically effective amount of the composition is increased over time to 200 mg/kg/day, to 400 mg/kg/day, to 800 mg/kg/day, or up to 1000 mg/kg/day.

22. The method of claim 1, further comprising monitoring the subject after the administration of the composition, comprising:
  a. observing muscle strength and control;
  b. observing differences in height and weight;
  c. observing mobility; and
  d. determining an improvement in condition of the subject if any of observations (a)-(c) are increased after administration of the composition and determining no improvement if any of observations (a)-(c) are the same or decreased after administration of the composition.

23. The method of claim 22, wherein if the determination of no improvement is made in step (d), the therapeutically effective amount of the composition is increased.

24. A method for the treatment of TK deficiency in a subject comprising:

a. obtaining a sample from the subject, said sample comprising nucleic acid;
b. performing sequence analysis of the TK2 gene in the nucleic acid of the subject;
c. determining the subject has TK2 deficiency when a homozygous mutation or compound heterozygous mutations in the TK2 gene is detected; and
d. administering a therapeutically effective amount of a composition comprising 2'-deoxycytidine-5'-monophosphate (dCMP), thymidine-5'-monophosphate (TMP), and mixtures thereof to the subject.

25. The method of claim 24, further comprising:
e. detecting the level of creatine kinase concentration in a sample from the subject;
f. performing a biopsy on skeletal muscle of the subject;
g. measuring mitochondrial DNA count in skeletal muscle of the subject; and
h. further determining and/or confirming the subject has TK2 deficiency if one or more of the following is detected: the levels of creatine kinase concentration are increased or elevated compared to healthy controls; the skeletal muscle of the subject comprises prominent variance in fiber size, variable sarcoplasmic vacuoles, variable increased connective tissue, ragged red fibers, and cytochrome c oxidase (COX) deficient fibers: and mitochondrial DNA levels are decreased compared to healthy controls.

* * * * *

UNITED STATES PATENT AND TRADEMARK OFFICE
CERTIFICATE OF CORRECTION

PATENT NO. : 10,292,996 B2
APPLICATION NO. : 15/082207
DATED : May 21, 2019
INVENTOR(S) : Michio Hirano et al.

Page 1 of 1

It is certified that error appears in the above-identified patent and that said Letters Patent is hereby corrected as shown below:

In the Specification

In Column 1, Lines 12-17:
Please change "This invention was made with government support under grant P01HD080642 awarded by the NIH. The Government has certain rights in this invention." to -- This invention was made with government support under grant HD080642 awarded by the National Institutes of Health. The Government has certain rights in this invention. --.

Signed and Sealed this
Tenth Day of September, 2019

Andrei Iancu
*Director of the United States Patent and Trademark Office*